US011634728B2

(12) United States Patent
Yu et al.

(10) Patent No.: US 11,634,728 B2
(45) Date of Patent: Apr. 25, 2023

(54) ADENO-ASSOCIATED VIRUS (AAV) VECTOR HAVING HYBRID HGF GENE INTRODUCED THERETO

(71) Applicant: HELIXMITH CO., LTD, Seoul (KR)

(72) Inventors: Seung Shin Yu, Seoul (KR); Jae Gyun Jeong, Seoul (KR); Jung Hun Lee, Seoul (KR); Su Bin Kim, Seoul (KR)

(73) Assignee: HELIXMITH CO., LTD, Seoul (KR)

( * ) Notice: Subject to any disclaimer, the term of this patent is extended or adjusted under 35 U.S.C. 154(b) by 366 days.

(21) Appl. No.: 16/956,926

(22) PCT Filed: Dec. 28, 2018

(86) PCT No.: PCT/KR2018/016937
§ 371 (c)(1),
(2) Date: Jun. 22, 2020

(87) PCT Pub. No.: WO2019/132624
PCT Pub. Date: Jul. 4, 2019

(65) Prior Publication Data
US 2021/0071199 A1    Mar. 11, 2021

(30) Foreign Application Priority Data
Dec. 29, 2017  (KR) ........................ 10-2017-0184738

(51) Int. Cl.
*C12N 15/86* (2006.01)
*A61K 48/00* (2006.01)
*C07K 14/475* (2006.01)

(52) U.S. Cl.
CPC .............. *C12N 15/86* (2013.01); *A61K 48/00* (2013.01); *C07K 14/475* (2013.01); *C07K 14/4753* (2013.01); *C12N 2750/14141* (2013.01); *C12N 2750/14143* (2013.01)

(58) Field of Classification Search
CPC .......... C12N 15/86; C12N 2750/14141; C12N 2750/14143; A61K 48/00; C07K 14/475; C07K 14/4753
See application file for complete search history.

(56) References Cited

U.S. PATENT DOCUMENTS

| | | | |
|---|---|---|---|
| 7,812,146 B2 * | 10/2010 | Kim .......................... | A61P 1/16 435/254.2 |
| 2005/0079581 A1 | 4/2005 | Kim et al. | |
| 2008/0181872 A1 | 7/2008 | Doroudchi | |
| 2009/0131350 A1 | 5/2009 | Kim et al. | |
| 2009/0258932 A1 | 10/2009 | Kim et al. | |
| 2010/0105878 A1 | 4/2010 | Kim et al. | |
| 2011/0166211 A1 | 7/2011 | Kim et al. | |
| 2012/0010273 A1 | 1/2012 | Kim et al. | |
| 2013/0211380 A1 | 8/2013 | Cabrera Aquino et al. | |
| 2014/0296142 A1 | 10/2014 | Kim et al. | |
| 2015/0111955 A1 | 4/2015 | High et al. | |
| 2015/0231208 A1 | 8/2015 | Jorgensen et al. | |
| 2016/0250291 A1 | 9/2016 | Jeong | |
| 2017/0143794 A1 | 5/2017 | Jorgensen et al. | |
| 2017/0281729 A1 | 10/2017 | Jeong et al. | |
| 2018/0055997 A1 | 3/2018 | Cabrera Aquino et al. | |
| 2018/0222955 A1 | 8/2018 | Kim et al. | |
| 2018/0282732 A1 | 10/2018 | Sah et al. | |
| 2019/0241632 A1 | 8/2019 | Kim et al. | |
| 2020/0157547 A1 | 5/2020 | Sah et al. | |

FOREIGN PATENT DOCUMENTS

| | | | | |
|---|---|---|---|---|
| CN | 1536085 | A | 10/2004 | |
| CN | 1876818 | A | 12/2006 | |
| EP | 3199182 | A1 | 8/2017 | |
| JP | 2005-520512 | A | 7/2005 | |
| JP | 2009-501009 | A | 1/2009 | |
| JP | 2011-516545 | A | 5/2011 | |
| JP | 2017-530128 | A | 10/2017 | |
| JP | 2017-197579 | A | 11/2017 | |
| JP | 2017-535266 | A | 11/2017 | |
| KR | 10-2014-0068148 | A | 6/2014 | |
| KR | 10-2015-0005521 | A | 1/2015 | |
| KR | 10-2017-0024614 | A | 3/2017 | |
| KR | 10-2017-0104129 | A | 9/2017 | |
| RU | 2015152546 | A | 6/2017 | |
| RU | 2016104614 | A | 8/2017 | |
| WO | WO-03078568 | A2 | 9/2003 | |
| WO | WO-2007058776 | A2 * | 5/2007 | ......... C07K 14/4753 |
| WO | WO-2009-125986 | A2 | 10/2009 | |
| WO | WO-2010/129021 | A1 | 11/2010 | |

OTHER PUBLICATIONS

Daya, Shyam, and Kenneth I. Berns. "Gene therapy using adeno-associated virus vectors." Clinical microbiology reviews 21.4 (2008): 583-593. (Year: 2008).*
International Search Report from corresponding PCT Application No. PCT/KR2018/016937, dated Apr. 19, 2019, with English Translation.
ESR of EP Patent Application No. 18894300.5 issued on Feb. 3, 2021.
Office Action of RU Patent Application No. 2020121178 dated May 18, 2021.
Office Action of JP Patent Application No. 2020-532995 dated May 18, 2021.
Office Action from corresponding Chinese Patent Application No. 201880085076.5 dated Dec. 26, 2022.
Liu, Z., et al.; "Effea of adenovirus-associated virus carrying kringle 1 domain of hepatocyte growth factor gene on the growth of human prostatic carcinoma xenograft in nude mouse bone", TUMOR, vol. 31, No. 7, Jul. 2011, pp. 585-590.

\* cited by examiner

*Primary Examiner* — Marcia S Noble
*Assistant Examiner* — Josephine M Gonzales
(74) *Attorney, Agent, or Firm* — Harness, Dickey & Pierce, P.L.C.

(57) ABSTRACT

The present invention relates to an AAV vector carrying a predetermined hybrid HGF gene sequence. Use of the AAV vector of the present invention allows a hybrid HGF gene to be delivered to a subject at a high delivery yield.

3 Claims, 8 Drawing Sheets

Specification includes a Sequence Listing.

ADENO-ASSOCIATED VIRUS (AAV) VECTOR HAVING HYBRID HGF GENE INTRODUCED THERETO

CROSS-REFERENCE TO RELATED APPLICATIONS

This application is a national phase application of PCT Application No. PCT/KR2018/016937, filed on 28 Dec. 2018, which claims the benefit of and priority to Korean Patent Application No. 10-2017-0184738, filed on 29 Dec. 2017. The entire disclosures of the applications identified in this paragraph are incorporated herein by references.

FIELD

The present invention relates to an AAV vector comprising a predetermined hybrid HGF gene sequence.

BACKGROUND

Gene therapy is a method in which therapeutic genes are delivered into cells of patients using gene recombinant technology to induce genetic mutations of target cells or express particular proteins, thereby treating genetic diseases, incurable diseases, and the like. Substances that carry the genes into living bodies are called carriers or vectors. Vectors are largely classified into viral vectors and non-viral vectors. Retroviruses and adenoviruses are representative types of viral vectors, and non-viral vectors include naked DNA, liposomes, and the like.

Hepatocyte growth factor (HGF) is one of the growth factors, and research on various functions of HGF is ongoing. Examples thereof are as follows: (1) the treatment of heart disease by HGF using liposome as carrier (Aoki et al., Angiogenesis induced by hepatocyte growth factor in non-infarcted myocardium and infracted myocardium: up-regulation of essential transcription factor for angiogenesis, etc. Gene Therapy 7:417-427, 2000); (2) the treatment of liver disease by HGF using AAV as carrier (Suzumura et al., Adeno-associated virus vector-mediated production of hepatocyte growth factor attenuates liver fibrosis in mice. Hepatol. Int. 2:80-88, 2008); (3) the treatment of diabetic peripheral neuropathy by HGF using naked DNA as carrier (Kessler et al., Double-blind, placebo-controlled study of HGF gene therapy in diabetic neuropathy. Annals of Clinical and Translational Neurology 2:465-478, 2015); and (4) the treatment of amyotrophic lateral sclerosis by HGF using naked DNA as carrier (Sufit et al., Open label study to assess the safety of VM202 in subjects with amyotrophic lateral sclerosis. Amyotroph Lateral Scler Frontotemporal Degener 18:269-278, 2017).

SUMMARY

Technical Problem

The present inventors have researched and endeavored to develop a gene delivery system with increased delivery efficiency of a hybrid HGF gene that simultaneously expresses hepatocyte growth factor (HGF) isoforms including flHGF and dHGF. As a result, the present inventors have established that gene delivery efficiency can be significantly improved when a downsized mutant of a previously known hybrid HGF gene and adeno-associated virus (AAV) as a gene delivery system are used, and thus have completed the present invention.

Therefore, an aspect of the present invention is to provide an adeno-associated virus (AAV) vector into which a foreign nucleic acid sequence consisting of a predetermined nucleotide sequence is introduced.

Another aspect of the present invention is to provide a transformant transformed with the above-described AAV vector.

Still another aspect of the present invention is to provide a composition comprising the above-described AAV vector for the prevention or treatment of diabetic peripheral neuropathy (DPN) or amyotrophic lateral sclerosis (ALS).

Other purposes and advantages of the present disclosure will become more obvious when taken with the following detailed description of the invention, claims, and drawings.

Technical Solution

In accordance with an aspect of the present invention, there is provided an adeno-associated virus (AAV) vector, into which a foreign nucleic acid sequence consisting of the nucleotide sequence of SEQ ID NO: 5 is introduced.

The present inventors have researched and endeavored to develop a gene delivery system with increased delivery efficiency of a hybrid HGF gene that simultaneously expresses hepatocyte growth factor (HGF) isoforms including flHGF and dHGF. As a result, the present inventors have established that gene delivery efficiency can be significantly improved when a downsized mutant of a previously known hybrid HGF gene and adeno-associated virus (AAV) as a gene delivery system are used.

As used herein, the term "hybrid HGF gene" refers to a gene sequence that simultaneously expresses two or more HGF isoforms by selective splicing. More specifically, the above-described two or more HGF isoforms include at least a full-length HGF (flHGF) isoform and a deleted variant HGF (dHGF) isoform.

Due to the degeneracy of codons or considering preferred codons in an organism where the HGF and dHGF genes are to be expressed, the hybrid HGF gene of the present invention may have various alterations in a coding region within the range that does not change the amino acid sequence of a protein expressed from the coding region, or may also have various alterations or modifications in a region other than the coding region within a range that does not affect the expression of the gene, and such altered or modified genes are also included in the scope of the present invention. Therefore, the present invention also includes a polynucleotide having substantially the same nucleotide sequence as the hybrid HGF gene of SEQ ID NO: 5, and fragments of the gene. The substantially the same polynucleotide means a polynucleotide having a sequence homology of at least 80%, preferably at least 90%, and the most preferably at least 95%.

The above-described hybrid HGF gene may include cDNA, corresponding to exons 1 to 18 of the human HGF gene and intron 4 of the human HGF gene, inserted between exons 4 and 5 of the cDNA, or fragments thereof. This sequence is known to be HGF-X7 consisting of the nucleotide sequence of SEQ ID NO: 6 (see KR 2017-0024614 (published on 7 Mar. 2017)). However, when inserted into an AAV vector, the above-described nucleotide sequence of SEQ ID NO: 6 has size-related limitations. The nucleotide sequence of SEQ ID NO: 5 of the present invention corresponds to a sequence showing significantly increased gene delivery efficiency among sequences which are downsized by removing a part of the sequence corresponding to the intron 4 fragment of the nucleotide sequence of SEQ ID NO: 6. Specifically, the delivery of the nucleotide sequence of SEQ ID NO: 5 to a subject through introduction into an AAV vector shows significantly increased gene delivery efficiency and expression efficiency compared with the use of the previously known HGF-X8 of SEQ ID NO: 7 through introduction into the AAV vector.

A polynucleotide may be delivered to a subject in a naked DNA state or a state of being contained in a gene delivery system. It has been known that a plasmid, a viral vector, or the like may be used as a gene delivery system, but, as described above, an adeno-associated virus (AAV) vector is used as a gene delivery system in the present invention.

AAV vectors may infect non-dividing cells and may infect various kinds of cells. Detailed descriptions of the construction and use of AAV vectors are disclosed in U.S. Pat. Nos. 5,139,941 and 4,797,368. The research results on AAV as a gene delivery system are disclosed in LaFace et al, Virology, 162:483486 (1988), Zhou et al., Exp. Hematol. (NY), 21:928-933 (1993); Walsh et al, J. Clin. Invest., 94:1440-1448 (1994); and Flotte et al., Gene Therapy, 2:29-37 (1995). Typically, AAV viruses are produced by co-transfection of a plasmid comprising a target gene sequence flanked by two AAV terminal repeats (McLaughlin et al., J. Virol., 62:1963-1973 (1988); and Samulski et al., J. Virol., 63:3822-3828 (1989)), an expression plasmid comprising a wild-type AAV coding sequence without terminal repeats, and a plasmid comprising an adenovirus helper gene (McCarty et al., J. Virol., 65:2936-2945 (1991)).

The AAV vector of the present invention may be used to deliver a foreign gene sequence into cells by various viral infection methods known in the art, and the methods are not particularly limited.

The AAV vector of the present invention has an AAV serotype selected from the group consisting of AAV1, AAV2, AAV3, AAV4, AAV5, AAV6, AAV7, AAV8, AAV9, AAV10, AAV11, AAV12, AAV13, AAV14, AAV15, and AAV16.

According to another aspect of the present invention, the present invention provides a transformant transformed with the above-described AAV vector.

The AAV vector of the present invention can be introduced into appropriate host cells, for example, mammalian cells, such as 293T cells, or insect cells, or the like, and the transformed host cells can be used to make mass-replication of DNA of the gene of the present invention or mass-production of a protein thereof.

In accordance with an aspect of the present invention, there is provided a composition comprising the above-described AAV vector for prevention or treatment of diabetic peripheral neuropathy (DPN) or amyotrophic lateral sclerosis (ALS).

As used herein, the term "prevention" refers to all acts of suppressing diabetic peripheral neuropathy or amyotrophic lateral sclerosis through administration of the composition of the present invention.

As used herein, the term "treatment" refers to (a) the delay or suppression of the progression/development of diabetic peripheral neuropathy or amyotrophic lateral sclerosis; (b) the relief of diabetic peripheral neuropathy or amyotrophic lateral sclerosis; and (c) the removal of diabetic peripheral neuropathy or amyotrophic lateral sclerosis.

The composition of the present invention may comprise a pharmaceutically acceptable carrier.

The pharmaceutically acceptable carrier contained in the pharmaceutical composition of the present invention is one that is typically used for formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oils. The pharmaceutical composition of the present invention may further comprise, in addition to the above ingredients, a lubricant, a wetting agent, a sweetening agent, a flavoring agent, an emulsifier, a suspending agent, a preservative, and the like. Suitable pharmaceutically acceptable carriers and preparations are described in detail in *Remington's Pharmaceutical Sciences* (19th ed., 1995).

The pharmaceutical composition of the present invention may be preferably administered parenterally, and for example, intravenous administration, intraperitoneal administration, intramuscular injection, subcutaneous administration, intrathecal administration, intracerebroventricular injection, intracerebral injection, or topical administration may be used.

The pharmaceutical composition of the present invention may be formulated and administered as an injection. The appropriate dose of the pharmaceutical composition of the present invention varies depending on factors, such as the method of formulation, the manner of administration, the patient's age, body weight, and gender, the severity of disease symptoms, the time of administration, the route of administration, the excretion rate, and response sensitivity. An ordinarily skilled practitioner can easily determine and prescribe the dose effective for desired treatment. According to an embodiment of the present invention, the AAV vector of the present invention is administered in an amount of $1 \times 10^8$ to $1 \times 10^{12}$ GC/site.

The pharmaceutical composition of the present invention is formulated using a pharmaceutically acceptable carrier and/or excipient according to a method that could be easily performed by a person having ordinary skills in the art to which the present invention pertains, and the pharmaceutical composition may be prepared into a unit dosage form, or may be inserted into a multi-dose container. The formulation may be in the form of a solution, suspension, or emulsion in an oily or aqueous medium, or an extract, a powder, granules, a tablet, or a capsule, and the formulation may further comprise a dispersant or a stabilizer.

In an embodiment of the present invention, the above-described diabetic peripheral neuropathy is polyneuropathy or focal neuropathy.

In an embodiment of the present invention, the foregoing polyneuropathy is at least one diabetic peripheral neuropathy selected from the group consisting of hyperglycemic neuropathy, distal symmetric polyneuropathy, autonomic neuropathy, acute sensory neuropathy, acute painful sensory neuropathy, and chronic sensorimotor neuropathy. More specifically, the foregoing focal neuropathy is at least one diabetic peripheral neuropathy selected from the group consisting of cranial neuropathy, truncal neuropathy, limb neuropathy, thoracolumbar radiculoneuropathy, and lumbosacral radiculoplexus neuropathy.

Advantageous Effects

Features and advantages of the present invention are summarized as follows.

(a) The present invention provides an adeno-associated virus (AAV) vector, into which a foreign nucleic acid sequence consisting of a predetermined nucleotide sequence is introduced.

(b) The present invention provides a transformant transformed with the above-described AAV vector.

(c) The present invention provides a composition comprising the above-described AAV vector for prevention or treatment of diabetic peripheral neuropathy (DPN) or amyotrophic lateral sclerosis (ALS).

(d) The use of the AAV vector of the present invention can deliver a hybrid HGF gene to a subject with high delivery efficiency.

DETAILED DESCRIPTION

Hereinafter, the present invention will be described in more detail with reference to examples. These examples are only for illustrating the present invention more specifically, and it will be apparent to those skilled in the art that the scope of the present invention is not limited by these examples according to the gist of the present invention.

EXAMPLES

Test Example 1: Preparation of HGF-X7 Derivatives

To construct an AAV vector expressing two isoforms of HGF, four derivatives were prepared from SEQ ID NO: 1 (pCK-HGF-X7) through site-directed mutagenesis. The detailed description of the method is as follows. First, PCR (site-directed mutagenesis kit, Stratagene, US) was performed using DNA of SEQ ID NO: 1 as a template. The primer sequences that were used are as follows.

TABLE 1

| d1 | Forward (SEQ ID NO: 8) | TCTCGGTATTTGTGGATCCTATTATGATCTT TTGTGTAAA |
|---|---|---|
|  | Reverse (SEQ ID NO: 9) | TTTACACAAAAGATCATAATAGGATCCACAA ATACCGAGA |
| d2 | Forward (SEQ ID NO: 10) | TCTCGGTATTTGTGGATCCTTTACTATTATA AACCAAAAC |
|  | Reverse (SEQ ID NO: 11) | GTTTTGGTTTATAATAGTAAAGGATCCACAA ATACCGAGA |

TABLE 1 -continued

| d3 | Forward (SEQ ID NO: 12) | TCTCGGTATTTGTGGATCCTAAGGTGTAAGA TGTTAAAGG |
|---|---|---|
|  | Reverse (SEQ ID NO: 13) | CCTTTAACATCTTACACCTTAGGATCCACAA ATACCGAGA |
| d4 | Forward (SEQ ID NO: 14) | TCTCGGTATTTGTGGATCCTTATAAGAAAAG CAATAAACA |
|  | Reverse (SEQ ID NO: 15) | TGTTTATTGCTTTTCTTATAAGGATCCACAA ATACCGAGA |

Figure 1:
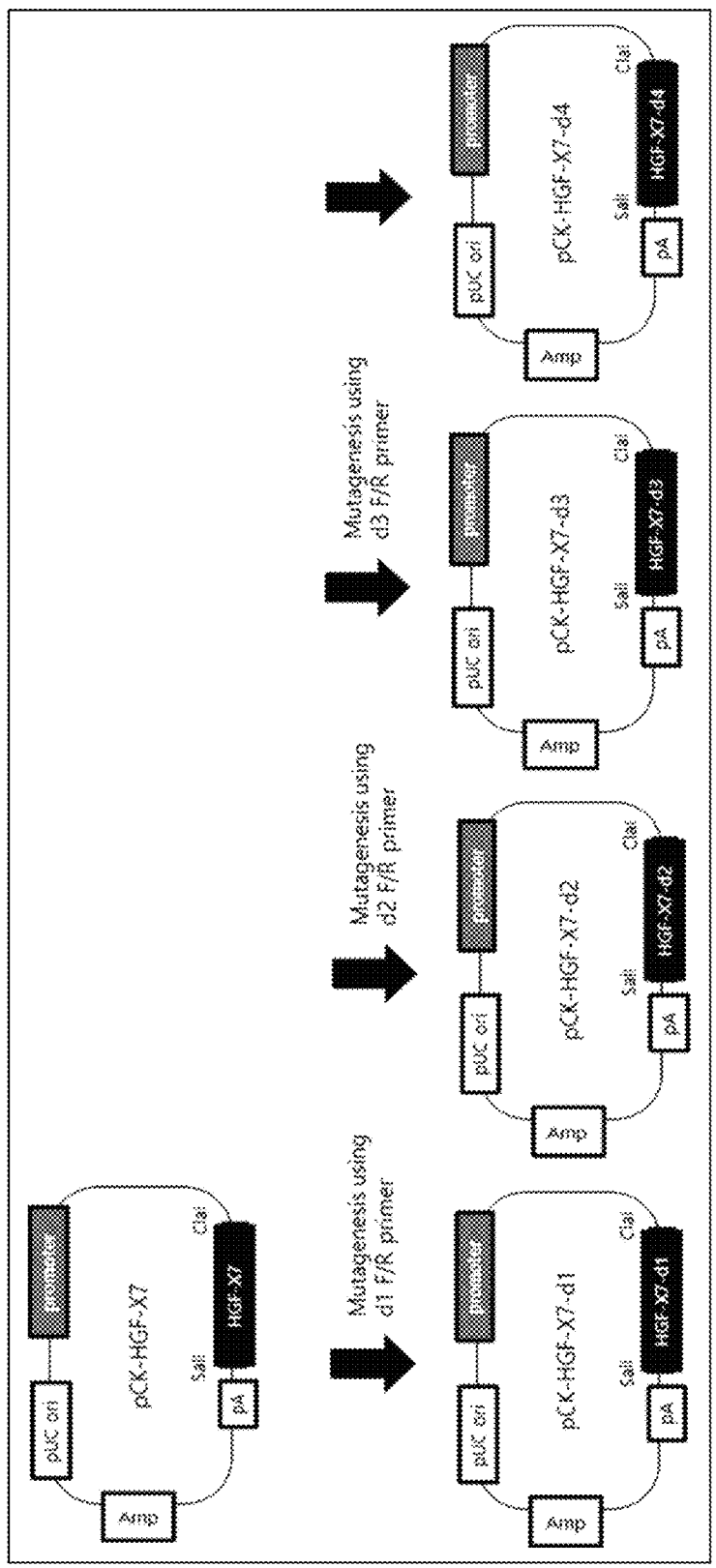
FIG. 1 is a schematic diagram showing a method for preparing downsized mutants of HGF-X7 from pCK-HGF-X7.

Out of the colonies obtained by delivering PCR products to C2C12 cells, colonies containing pCK-HGF-X7-d1, pCK-HGF-X7-d2, pCK-HGF-X7-d3, and pCK-HGF-X7-d4 were selected, and plasmid DNA was extracted therefrom (see FIG. 1).

Test Example 2: Construction of pCA-HGF-X7 Derivatives

Figure 2:
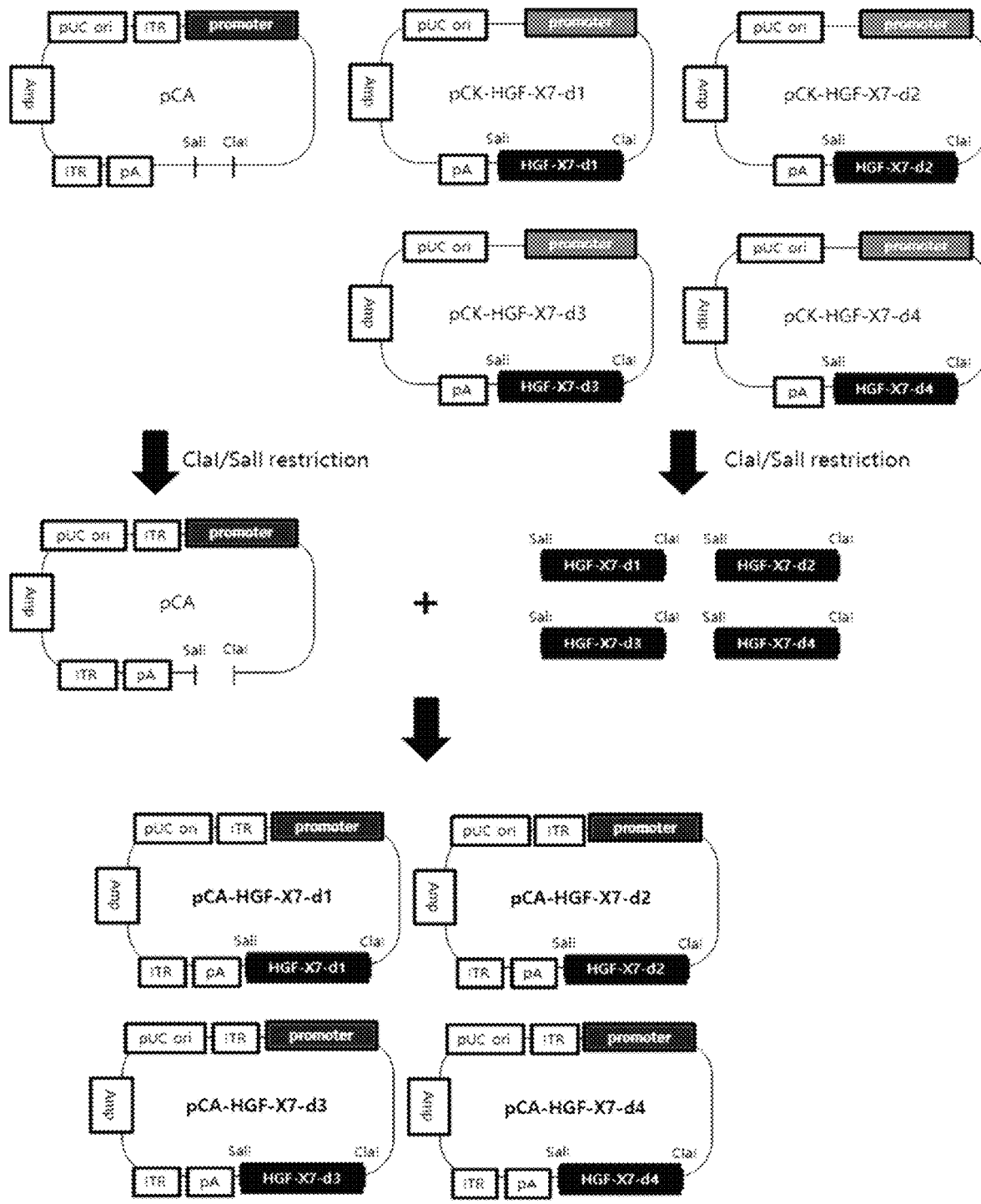
FIG. 2 is a schematic diagram showing a method for cloning downsized mutants of HGF-X7 into pCA vectors.

For the production of AAVs containing the four derivatives obtained in Test Example 1, theses derivatives were cloned into respective pCA vectors (AAV helper-free system, Agilent, USA). First, pCK-HGF-X7-d1, pCK-HGF-X7-d2, pCK-HGF-X7-d3, and pCK-HGF-X7-d4 in Test Example 1 were digested with ClaI and SalI restriction enzymes to give four types of fragments, HGF-X7-d1, HGF-X7-d2, HGF-X7-d3, and HGF-X7-d4. The pCA vectors were also digested with ClaI and SalI restriction enzymes, and then were subjected to ligation with the four types of fragments, HGF-X7-d1, HGF-X7-d2, HGF-X7-d3, and HGF-X7-d4, thereby constructing pCA-HGF-X7-d1, pCA-HGF-X7-d2, pCA-HGF-X7-d3, and pCA-HGF-X7-d4, respectively (see FIG. 2).

Test Example 3: Production of AAV-pCA-HGF-X7 Derivatives

The respective plasmid DNAs constructed in Test Example 2 were used to produce AAVs. For the production of AAVs, 239T cells (ATCC) were prepared the day before and stabilized for 24 hours. The 293T cells were transfected with the plasmid DNAs constructed in Test Example 2, pHelper as DNA necessary for AAV production, and pAAV-RC (AAV helper-free system, Agilent, USA), and after three days, AAVs were collected. The titers of the collected AAVs were measured using a titration kit (AAVpro Titration Kit, Takara, JP). AAVs were produced using a total of four serotypes (AAV1, AAV2, AAV5, and AAV6).

Test Example 4: Verification of hHGF Expression or not of AAV-pCA-HGF-X7 Derivatives 4-1. Methods Out of the AAVs produced in Test Example 3, AAV2-pCA-HGF-X7-d3 and AAV2-pCA-HGF-X7-d4 were tested to investigate hHGF expression. First, C2C12 cells (ATCC) were plated at 8×104 cells/well in a 12-well plate, and the cells were stabilized for 24 hours. The C2C12 cells were respectively infected with equivalent titers of AAV2-pCA-HGF-X7-d3 and AAV2-pCA-HGF-X7-d4. The supernatant was collected two days after infection, and the amount of HGF protein was analyzed by performing HGF ELISA (R&D systems, US).

4-2. Results

Figure 3:
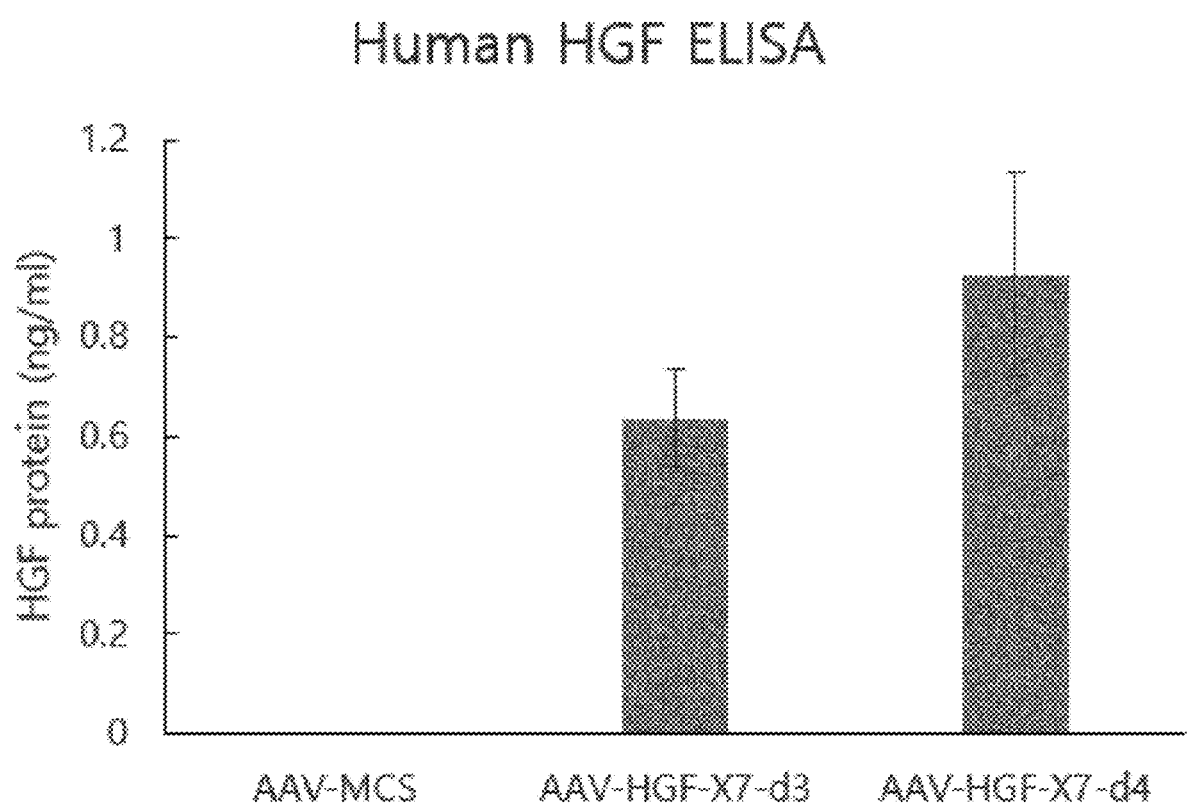
FIG. 3 is a graph showing the expression level of HGF protein in C2C12 cells infected with AAV-pCA-HGF-X7-d3 and AAV-pCA-HGF-X7-d4, respectively.

As a test result, it was confirmed that both AAV2-pCA-HGF-X7-d3 and AAV2-pCA-HGF-X7-d4 expressed the HGF protein. Especially, it was confirmed that the HGF expression level by AAV2-pCA-HGF-X7-d4 was higher than that by AAV2-pCA-HGF-X7-d3 (see FIG. 3).

Test Example 5: Comparison of hHGF Expression Between AAV-pCA-HGF-X7-d4 and AAV-pCA-HGF-X8

5-1. Methods

AAV2-pCA-HGF-X7-d4 and AAV2-pCA-HGF-X8 were tested to compare the hHGF expression level as follows. First, C2C12 cells (ATCC) were plated at $8 \times 10^4$ cells/well in a 12-well plate, and the cells were stabilized for 24 hours. The C2C12 cells were respectively infected with equivalent titers of AAV2-pCA-HGF-X7-d4 and AAV2-pCA-HGF-X8. The supernatant was collected two days after the infection, and the amount of HGF protein was analyzed by performing HGF ELISA (R&D systems, US).

5-2 Results

Figure 4:
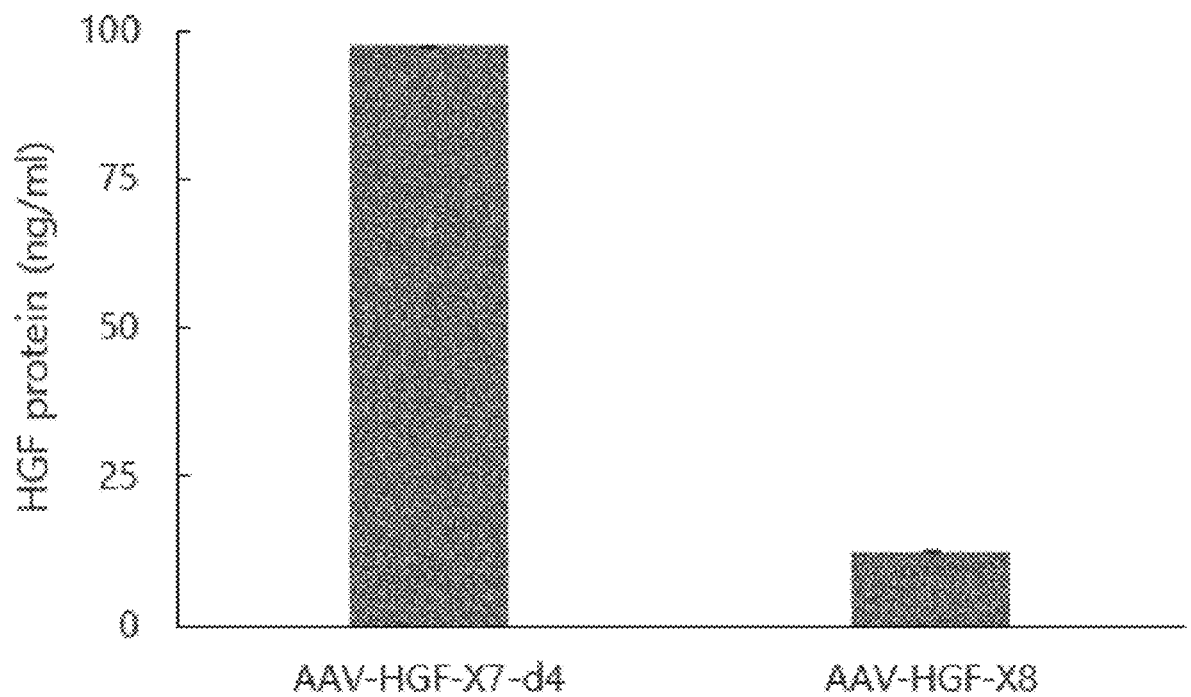
FIG. 4 is a graph showing the expression level of HGF protein in C2C12 cells infected with AAV2-pCA-HGF-X7-d4 and AAV2-pCA-HGF-X8.

As a test result, it was confirmed that both AAV2-pCA-HGF-X7-d4 and AAV2-pCA-HGF-X8 expressed HGF protein, but AAV2-pCA-HGF-X7-d4 showed a significantly higher HGF expression level by about 9-10 times when compared with AAV2-pCA-HGF-X8 (see FIG. 4).

Test Example 6: Effect of Intramuscular Injection of AAV-pCA-HGF-X7-d4 in ALS Mouse Models 6-1. Methods 6-1-1. Fabrication of ALS Mouse Models and Gene Delivery The widely used hSOD1-G93A models were used as ALS models. The models were obtained through crossbreeding of ALS mice (Jackson Laboratory, US), subjected to genotyping, and then examined for the presence or absence of Tg. Ten weeks after birth, the mice were organized into two groups (Tg-AAV6-MCS: 8 animals, Tg-AAV6-pCA-HGF-X7-d4: 7 animals). Non-Tg individuals were sorted out and used as negative control (non-Tg: 5 animals). The mice aged 90 days were administered with AAV at $1 \times 10^8$ GC/site via the thigh muscle, anterior tibial muscle, and gastrocnemius muscle. A total of $3 \times 10^8$ GC/head was administered.

6-1-2. Measurement of Disease Progression Rate, Survival Rate, and Weight

For the evaluation of efficacy, the disease progression rate and the weight were determined, and whether or not the individuals survived was observed. ALS disease eventually causes death according to the progression of the disease, and thus the above three indicators are representative analysis criteria that are widely used in ALS animal tests. The disease progression rate was measured according to the following standards and numerically expressed.

Symptom Score 5 points: normal 4 points: lower body balance was maintained for 1-2 seconds when mouse tail was grasped.

3 points: lower body balance was maintained for less than 1 second when mouse tail was caught, but walking was normal 2 points: lower body balance was not maintained with legs dragging 1 point: lower body balance was not maintained, walking on tops of feet.

0 points: Death 6-2 Results

Figure 5:
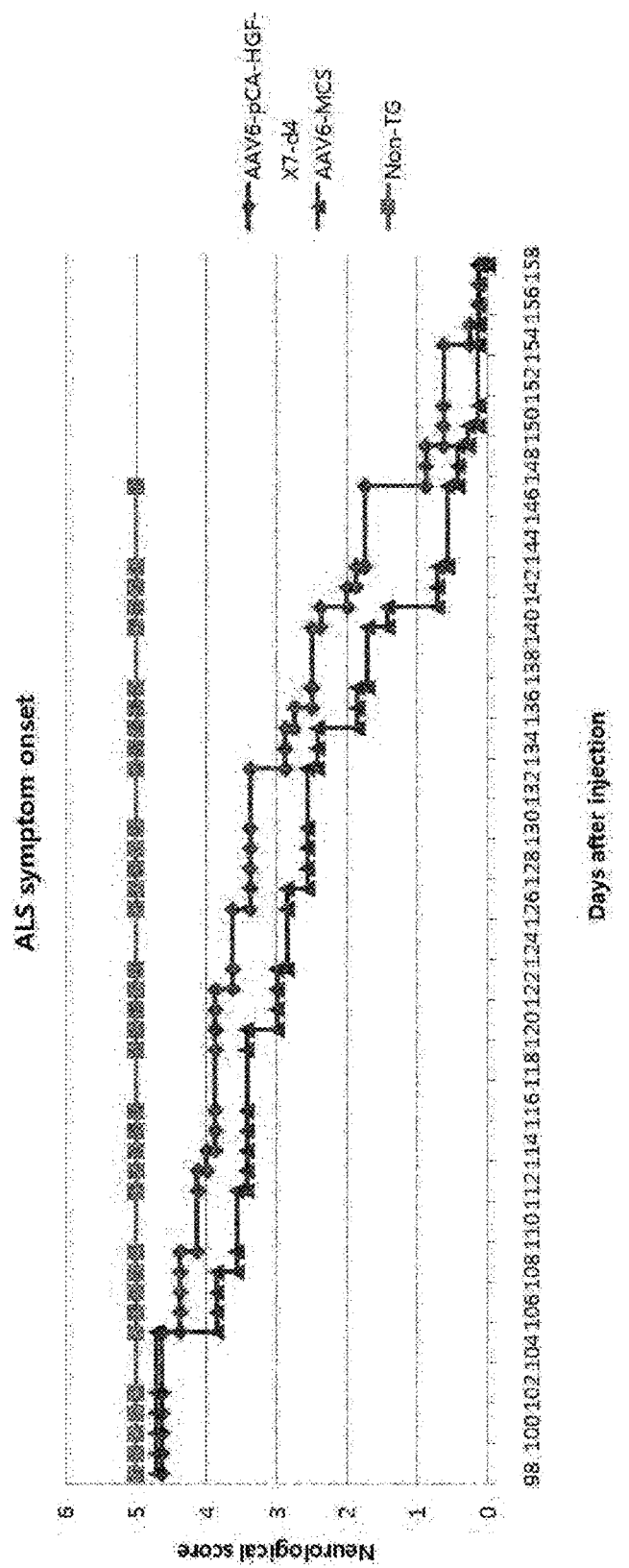
FIG. 5 is a graph showing a delay of progression of disease after intramuscular injection of AAV6-pCA-HGF-X7-d4 in ALS mice.

It was confirmed that the disease worsened over time in ALS mice (AAV6-MCS administration group). However, it was confirmed that the progression of the disease was delayed by the administration of AAV6-pCA-HGF-X7-d4. When the progression of the disease was numerically expressed, ALS mice had an average symptom score of 2.36 throughout the test period, whereas the group administered with AAV6-pCA-HGF-X7-d4 showed an average symptom score of 2.88, indicating a higher value than that for the ALS mice (AAV6-MCS administration group) (see FIG. 5).

Figure 6:
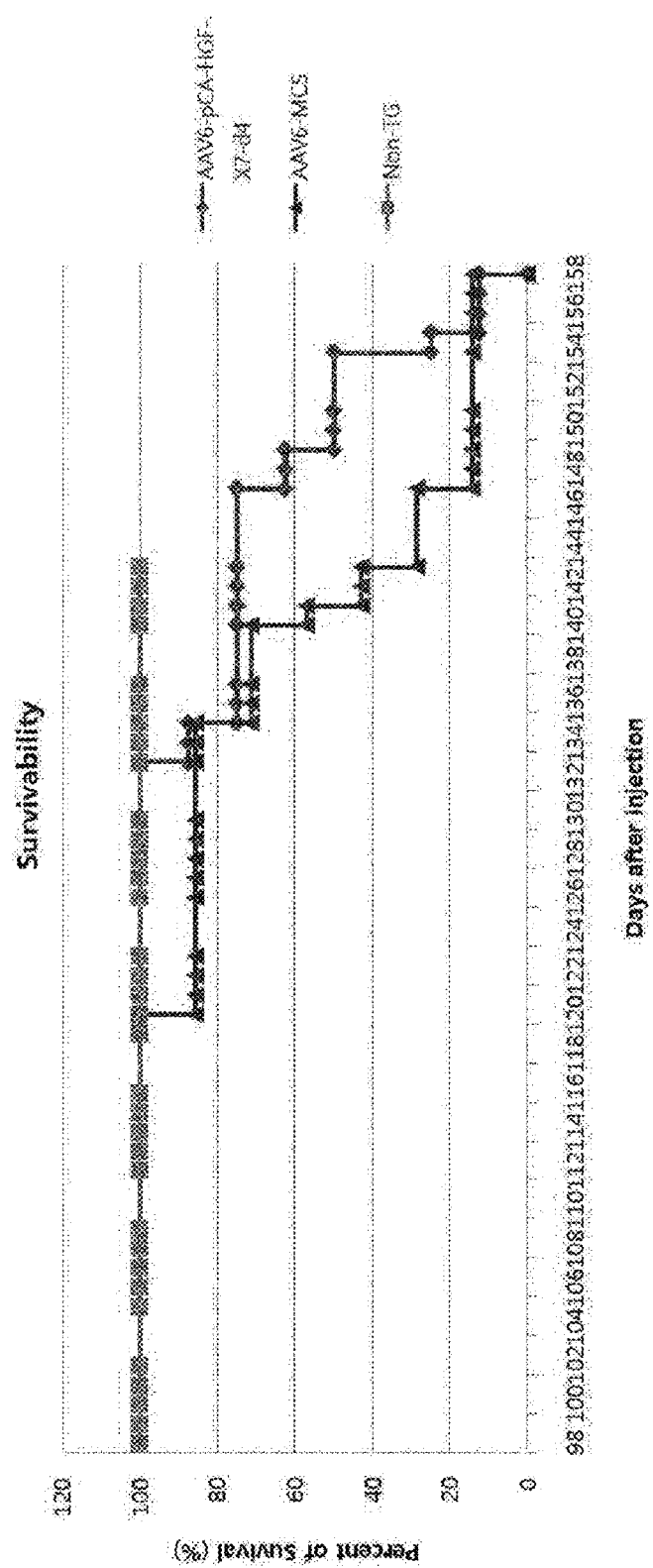
FIG. 6 is a graph showing the degree of improvement in survival rate after intramuscular injection of AAV6-pCA-HGF-X7-d4 in ALS mice.

It was also confirmed that the administration of AAV6-pCA-HGF-X7-d4 led to a notable improvement effect in survival rate. With regard thereto, the group administered with AAV6-MCS survived an average of 139 days after birth, whereas the group administered with AAV6-pCA-HGF-X7-d4 survived an average of 147 days, indicating an increase of about 8 days (see FIG. 6).

Figure 7:
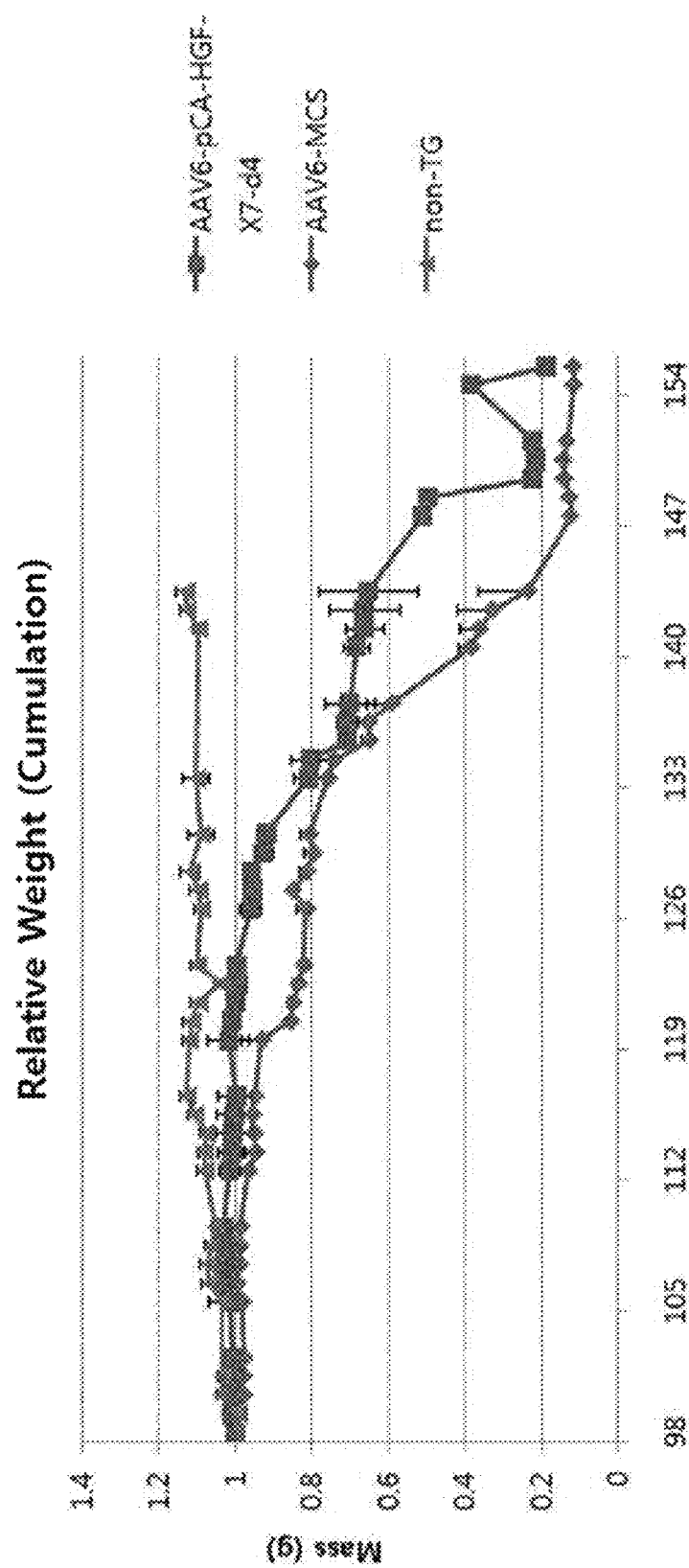
FIG. 7 is a graph showing the degree of slowdown in weight loss after intramuscular injection of AAV6-pCA-HGF-X7-d4 in ALS mice.

It was lastly confirmed that ALS mice (AAV6-MCS) had a noticeable increase in weight loss due to muscle loss, but the administration of AAV6-pCA-HGF-X7-d4 slowed weight loss. That is, it was confirmed through a relative comparison of weight that the ALS mice had an average weight change of about 34% from the time of administration to the end of the test, but administration of AAV6-pCA-HGF-X7-d4 showed an average weight change of 22%, indicating slower weight loss (see FIG. 7).

Test Example 7: Effect of Intrathecal Administration of AAV-pCA-HGF-X7-d4 in ALS Mouse Models 7-1. Methods 7-1-1. Fabrication of ALS Mouse Models and Gene Delivery The widely used hSOD1-G93A models were used as ALS models. The models were obtained through crossbreeding of ALS mice (Jackson Laboratory, US), subjected to genotyping, and then examined for the presence or absence of Tg. Individuals retaining a predetermined level of mutant gene were selected and used in the test. Non-Tg individuals were used as a negative control (13 animals). The Tg individuals were organized into a Tg-AAV1-MCS group and a Tg-AAV1-pCA-HGF-X7-d4 group, containing 14 and 16 animals, respectively. At 60 days of age, the mice were intrathecally administered once with AAV at $5 \times 109$ GC/site.

7-1-2. Survival Rate Investigation and Behavioral Test Analysis

For a detailed examination of efficacy, a survival rate, one of the most important indicators in ALS, was investigated, and for the examination of individual motor ability in ALS disease-afflicted individuals, rotarod and hanging-wire tests were carried out. In addition, for the examination of muscular function strength, grip strength was measured.

The survival rate was investigated by checking the survival or death of the individuals every day. As for the rotarod test, an acceleration method was used, in which a mouse was placed on a rotating rod and then the time was measured for how long the mouse spent on the rotating rod, and especially, the speed of the rotating rod was accelerated over time.

As for the hanging-wire test, a mouse was placed on a structure with a lattice pattern, and then the structure was inverted, and the time that the individual spent hanging on to the structure upside down was measured.

As for the grip strength test, the front and back feet of a mouse were placed on a strength measuring device, and then the muscular strength was measured.

Data are expressed as mean±SEM, and statistical analysis for each data set was performed using one-way ANOVA for each time, followed by Tukey post-hoc test (*: p<0.05, : p<0.01, *: p<0.001, ****: p<0.0001)

7-2 Results

It was confirmed that a treatment effect was observed in the intrathecal administration of AAV1-pCA-HGF-X7-d4. First, as a result of survival investigation, the AAV1-pCA-HGF-X7-d4 administration group showed a significant survival increase compared with the AAV1-MCS administration group. It was confirmed that the mice had an average lifespan of 144 days when administered with AAV1-MCS, whereas individuals administered with AAV1-pCA-HGF-X7-d4 showed an average lifespan of 160 days, indicating an increase of about 16 days.

Figure 8:
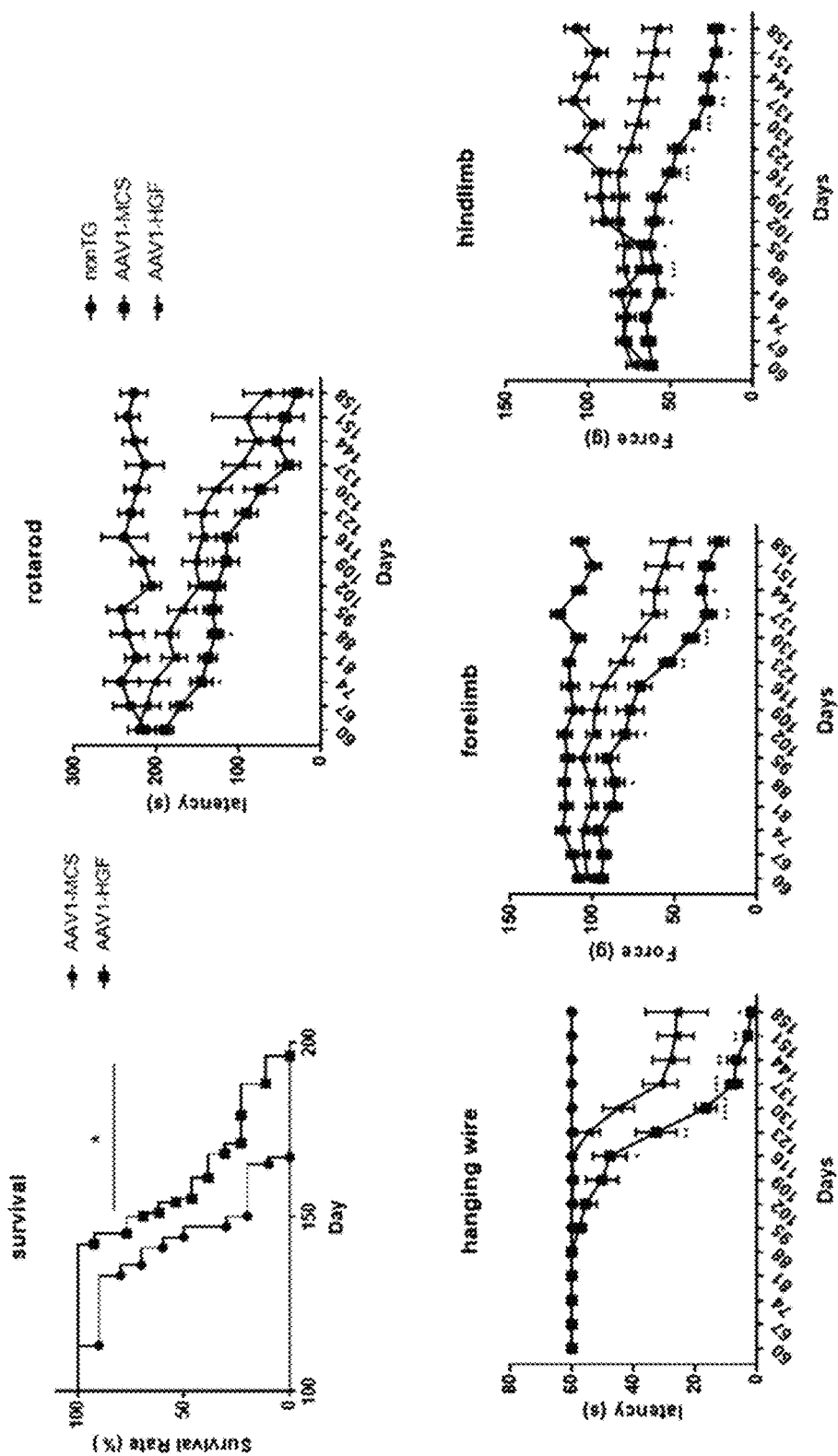
FIG. 8 depicts graphs showing the results of survival rate investigation and behavioral test analysis after intrathecal administration of AAV1-pCA-HGF-X7-d4 in ALS mice.

Motor ability was observed to be actually enhanced. In the rotarod test, the negative control remained on the rotarod for an average of 226 seconds, whereas the time was significantly decreased to 112 seconds in the Tg-AAV1-MCS group. However, the time was improved to an average of 151 seconds for the test group administered with AAV1-pCA-HGF-X7-d4. Similar treatment effects were also observed in the hanging-wire and grip strength tests. In particular, at the last stage of disease progression (on day 137 after birth), the time spent hanging from the wire was about 31 seconds in the AAV1-pCA-HGF-X7-d4 administration group, indicating a great increase compared with about 7 seconds in the AAV1-MCS administration group. Also in the grip strength measurement results, the AAV1-MCS administration group showed a strength of approximately 28 g, but the strength was significantly increased to 66 g in the pCA-HGF-X7-d4 administration group (see FIG. 8).

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An adeno-associated virus (AAV) vector, comprising a foreign nucleic acid sequence consisting of:
    (a) the nucleotide sequence set forth in SEQ ID NO: 5; or
    (b) a codon-modified nucleotide sequence having homology of at least 80% to the nucleotide sequence set forth in SEQ ID NO: 5, wherein said codon-modified nucleotide sequence encodes the same amino acid sequence as the coding region of the nucleotide sequence set forth in SEQ ID NO: 5.

2. An isolated recombinant cell transformed with the AAV vector of claim 1.

3. A composition comprising the AAV vector of claim 1.

* * * * *

SEQUENCE LISTING

```
<160> NUMBER OF SEQ ID NOS: 15

<210> SEQ ID NO 1
<211> LENGTH: 7377
<212> TYPE: DNA
<213> ORGANISM: Artificial Sequence
<220> FEATURE:
<223> OTHER INFORMATION: pCK-HGF-X7

<400> SEQUENCE: 1
cgcgttgaca ttgattattg actagttatt aatagtaatc aattacgggg tcattagttc      60
atagcccata tatggagttc cgcgttacat aacttacggt aaatggcccg cctggctgac     120
cgcccaacga cccccgccca ttgacgtcaa taatgacgta tgttcccata gtaacgccaa     180
tagggacttt ccattgacgt caatgggtgg agtatttacg gtaaactgcc cacttggcag     240
tacatcaagt gtatcatatg ccaagtccgc ccccctattga cgtcaatgac ggtaaatggc     300
ccgcctggca ttatgcccag tacatgacct tacgggactt tcctacttgg cagtacatct     360
acgtattagt catcgctatt accatggtga tgcggttttg gcagtacacc aatgggcgtg     420
gatagcggtt tgactcacgg ggatttccaa gtctccaccc cattgacgtc aatgggagtt     480
tgttttggca ccaaaatcaa cgggactttc caaaatgtcg taataacccc gccccgttga     540
cgcaaatggg cggtaggcgt gtacggtggg aggtctatat aagcagagct cgtttagtga     600
accgtcagat cgcctggaga cgccatccac gctgttttga cctccataga agacaccggg     660
accgatccag cctccgcggc cgggaacggt gcattggaac gcggattccc cgtgccaaga     720
gtgacgtaag taccgcctat agactctata ggcacacccc tttggctctt atgcatgcta     780
tactgttttt ggcttggggc ctatacaccc ccgcttcctt atgctatagg tgatggtata     840
gcttagccta taggtgtggg ttattgacca ttattgacca ctcccctatt ggtgacgata     900
ctttccatta ctaatccata acatggctct ttgccacaac tatctctatt ggctatatgc     960
caatactctg tccttcagag actgacacgg actctgtatt tttacaggat ggggtcccat    1020
ttattattta caaattcaca tatacaacaa cgccgtcccc cgtgcccgca gtttttatta    1080
aacatagcgt gggatctcca cgcgaatctc gggtacgtgt tccggacatg ggctcttctc    1140
cggtagcggc ggagcttcca catccgagcc ctggtcccat gcctccagcg gctcatggtc    1200
gctcggcagc tccttgctcc taacagtgga ggccagactt aggcacagca caatgcccac    1260
caccaccagt gtgccgcaca aggccgtggc ggtagggtat gtgtctgaaa atgagctcgg    1320
```

```
agattgggct cgcaccgctg acgcagatgg aagacttaag gcagcggcag aagaagatgc    1380
aggcagctga gttgttgtat tctgataaga gtcagaggta actcccgttg cggtgctgtt    1440
aacggtggag ggcagtgtag tctgagcagt actcgttgct gccgcgcgcg ccaccagaca    1500
taatagctga cagactaaca gactgttcct ttccatgggt cttttctgca gtcaccgtcc    1560
ttgacacgaa gcttgctagc accatgtggg tgaccaaact cctgccagcc ctgctgctgc    1620
agcatgtcct cctgcatctc ctcctgctcc ccatcgccat ccctatgca gagggacaaa     1680
ggaaaagaag aaatacaatt catgaattca aaaaatcagc aaagactacc ctaatcaaaa    1740
tagatccagc actgaagata aaaccaaaa aagtgaatac tgcagaccaa tgtgctaata     1800
gatgtactag gaataaagga cttccattca cttgcaaggc ttttgttttt gataaagcaa    1860
gaaaacaatg cctctggttc cccttcaata gcatgtcaag tggagtgaaa aaagaatttg    1920
gccatgaatt tgacctctat gaaaacaaag actacattag aaactgcatc attggtaaag    1980
gacgcagcta caagggaaca gtatctatca ctaagagtgg catcaaatgt cagccctgga    2040
gttccatgat accacacgaa cacaggtaag aacagtatga agaaaagaga tgaagcctct    2100
gtcttttta catgttaaca gtctcatatt agtccttcag aataattcta caatcctaaa     2160
ataacttagc caacttgctg aattgtatta cggcaaggtt tatatgaatt catgactgat    2220
atttagcaaa tgattaatta atatgttaat aaaatgtagc caaaacaata tcttacctta    2280
atgcctcaat ttgtagatct cggtatttgt ggatcctggg taggaaacac atttgaatgg    2340
tatttactaa gatactaaaa tccttggact tcactctaat tttagtgcca tttagaactc    2400
aaggtctcag taaaagtaga aataaagcct gttaacaaaa cacaaactga atattaaaaa    2460
tgtaactgga ttttcaaaga aatgttact ggtattacct gtagatgtat attctttatt     2520
atgatctttt gtgtaaagtc tggcagacaa atgcaatatc taattgttga gtccaatatc    2580
acaagcagta caaagtata aaaaagactt ggccttttct aatgtgttaa aatactttat      2640
gctggtaata acactaagag tagggcacta gaaattttaa gtgaagataa tgtgttgcag    2700
ttactgcact caatggctta ctattataaa ccaaaactgg gatcactaag ctccagtcag    2760
tcaaaatgat caaaattatt gaagagaata agcaattctg ttctttatta ggacacagta    2820
gatacagact acaaagtgga gtgtgcttaa taagaggtag catttgttaa gtgtcaatta    2880
ctctattatc ccttggagct tctcaaaata accatataag gtgtaagatg ttaaaggtta    2940
tggttacact cagtgcacag gtaagctaat aggctgagag aagctaaatt acttactggg    3000
gtctcacagt aagaaagtga gctgaagttt cagcccagat ttaactggat tctgggctct    3060
ttattcatgt tacttcatga atctgtttct caattgtgca gaaaaaaggg ggctatttat    3120
aagaaaagca ataacaaac aagtaatgat ctcaaataag taatgcaaga aatagtgaga     3180
tttcaaaatc agtggcagcg atttctcagt tctgtcctaa gtggccttgc tcaatcacct    3240
gctatctttt agtggagctt tgaaattatg tttcagacaa cttcgattca gttctagaat    3300
gtttgactca gcaaattcac aggctcatct ttctaacttg atggtgaata tggaaattca    3360
gctaaatgga tgttaataaa attcaaacgt tttaaggaca gatggaaatg acagaatttt    3420
aaggtaaaat atatgaagga atataagata aaggattttt ctaccttcag caaaaacata    3480
cccactaatt agtaaaatta ataggcgaaa aaaagttgca tgctcttata ctgtaatgat    3540
tatcatttta aaactagctt tttgccttcg agctatcggg gtaaagacct acaggaaaac    3600
tactgtcgaa atcctcgagg ggaagaaggg ggaccctggt gtttcacaag caatccagag    3660
gtacgctacg aagtctgtga cattcctcag tgttcagaag ttgaatgcat gacctgcaat    3720
```

```
ggggagagtt atcgaggtct catggatcat acagaatcag gcaagatttg tcagcgctgg    3780
gatcatcaga caccacaccg gcacaaattc ttgcctgaaa gatatcccga caagggcttt    3840
gatgataatt attgccgcaa tcccgatggc cagccgaggc catggtgcta tactcttgac    3900
cctcacaccc gctgggagta ctgtgcaatt aaaacatgcg ctgacaatac tatgaatgac    3960
actgatgttc ctttggaaac aactgaatgc atccaaggtc aaggagaagg ctacaggggc    4020
actgtcaata ccatttggaa tggaattcca tgtcagcgtt gggattctca gtatcctcac    4080
gagcatgaca tgactcctga aaatttcaag tgcaaggacc tacgagaaaa ttactgccga    4140
aatccagatg ggtctgaatc accctggtgt tttaccactg atccaaacat ccgagttggc    4200
tactgctccc aaattccaaa ctgtgatatg tcacatggac aagattgtta cgtgggaat    4260
ggcaaaaatt atatgggcaa cttatcccaa acaagatctg gactaacatg ttcaatgtgg    4320
gacaagaaca tggaagactt acatcgtcat atcttctggg aaccagatgc aagtaagctg    4380
aatgagaatt actgccgaaa tccagatgat gatgctcatg gaccctggtg ctacacggga    4440
aatccactca ttccttggga ttattgccct atttctcgtt gtgaaggtga taccacacct    4500
acaatagtca atttagacca tcccgtaata tcttgtgcca aaacgaaaca attgcgagtt    4560
gtaaatggga ttccaacacg aacaaacata ggatggatgg ttagtttgag atacagaaat    4620
aaacatatct gcggaggatc attgataaag gagagttggg ttcttactgc acgacagtgt    4680
ttcccttctc gagacttgaa agattatgaa gcttggcttg gaattcatga tgtccacgga    4740
agaggagatg agaaatgcaa acaggttctc aatgtttccc agctggtata tggccctgaa    4800
ggatcagatc tggtttttaat gaagcttgcc aggcctgctg tcctggatga ttttgttagt    4860
acgattgatt tacctaatta tggatgcaca attcctgaaa agaccagttg cagtgtttat    4920
ggctggggct acactggatt gatcaactat gatggcctat tacgagtggc acatctctat    4980
ataatgggaa atgagaaatg cagccagcat catcgaggga aggtgactct gaatgagtct    5040
gaaatatgtg ctggggctga aaagattgga tcaggaccat gtgaggggga ttatggtggc    5100
ccacttgttt gtgagcaaca taaaatgaga atggttcttg gtgtcattgt tcctggtcgt    5160
ggatgtgcca ttccaaatcg tcctggtatt tttgtccgag tagcatatta tgcaaaatgg    5220
atacacaaaa ttattttaac atataaggta ccacagtcat agcggccgct ctagagggcc    5280
cgtttaaacc cgctgatcag cctcgactgt gccttctagt tgccagccat ctgttgtttg    5340
cccctccccc gtgccttcct tgaccctgga aggtgccact cccactgtcc tttcctaata    5400
aaatgaggaa attgcatcgc attgtctgag taggtgtcat tctattctgg ggggtggggt    5460
ggggcaggac agcaagggg aggattggga agacaatagc aggcatgctg gggagtcgaa    5520
attcagaaga actcgtcaag aaggcgatag aaggcgatgc gctgcgaatc gggagcggcg    5580
ataccgtaaa gcacgaggaa gcggtcagcc cattcgccgc caagctcttc agcaatatca    5640
cgggtagcca acgctatgtc ctgatagcgg tccgccacac ccagccggcc acagtcgatg    5700
aatccagaaa agcggccatt ttccaccatg atattcggca agcaggcatc gccatgggtc    5760
acgacgagat cctcgccgtc gggcatgctc gccttgagcc tggcgaacag ttcggctggc    5820
gcgagcccct gatgctcttc gtccagatca tcctgatcga caagaccggc ttccatccga    5880
gtacgtgctc gctcgatgcg atgtttcgct tggtggtcga atgggcaggt agccggatca    5940
agcgtatgca gccgccgcat tgcatcagcc atgatggata cttctcggc aggagcaagg    6000
tgagatgaca ggagatcctg cccgggcact tcgcccaata gcagccagtc ccttcccgct    6060
```

```
tcagtgacaa cgtcgagcac agctgcgcaa ggaacgcccg tcgtggccag ccacgatagc   6120
cgcgctgcct cgtcttgcag ttcattcagg gcaccggaca ggtcggtctt gacaaaaaga   6180
accgggcgcc cctgcgctga cagccggaac acggcggcat cagagcagcc gattgtctgt   6240
tgtgcccagt catagccgaa tagcctctcc acccaagcgg ccggagaacc tgcgtgcaat   6300
ccatcttgtt caatcatgcg aaacgatcct catcctgtct cttgatcaga tcttgatccc   6360
ctgcgccatc agatccttgg cggcaagaaa gccatccagt ttactttgca gggcttccca   6420
accttaccag agggcgcccc agctggcaat tccggttcgc ttgctgtcca taaaaccgcc   6480
cagtctagct atcgccatgt aagcccactg caagctacct gctttctctt tgcgcttgcg   6540
ttttcccttg tccagatagc ccagtagctg acattcatcc ggggtcagca ccgtttctgc   6600
ggactggctt tctacgtgaa aaggatctag gtgaagatcc tttttgataa tctcatgacc   6660
aaaatccctt aacgtgagtt ttcgttccac tgagcgtcag accccgtaga aagatcaaa    6720 ggatcttctt gagatccttt ttttctgcgc gtaatctgct gcttgcaaac aaaaaaacca   6780
ccgctaccag cggtggtttg tttgccggat caagagctac caactctttt tccgaaggta   6840
actggcttca gcagagcgca gataccaaat actgttcttc tagtgtagcc gtagttaggc   6900
caccacttca agaactctgt agcaccgcct acatacctcg ctctgctaat cctgttacca   6960
gtggctgctg ccagtggcga taagtcgtgt cttaccgggt tggactcaag acgatagtta   7020
ccggataagg cgcagcggtc gggctgaacg gggggttcgt gcacacagcc cagcttggag   7080
cgaacgacct acaccgaact gagatacccta cagcgtgagc tatgagaaag cgccacgctt   7140
cccgaaggga gaaaggcgga caggtatccg gtaagcggca gggtcggaac aggagagcgc   7200
acgagggagc ttccaggggg aaacgcctgg tatctttata gtcctgtcgg gtttcgccac   7260
ctctgacttg agcgtcgatt tttgtgatgc tcgtcagggg gcggagcct  atggaaaaac   7320 gccagcaacg cggccttttt acggttcctg gccttttgct ggccttttgc tcacatg       7377
```

<210> SEQ ID NO 2
<211> LENGTH: 3479
<212> TYPE: DNA
<213> ORGANISM: Artificial Sequence
<220> FEATURE:
<223> OTHER INFORMATION: HGF-X7-d1

<400> SEQUENCE: 2

```
atgtgggtga ccaaactcct gccagccctg ctgctgcagc atgtcctcct gcatctcctc     60
ctgctcccca tcgccatccc ctatgcagag ggacaaagga aaagaagaa  tacaattcat   120 gaattcaaaa aatcagcaaa gactacccta atcaaaatag atccagcact gaagataaaa   180
accaaaaaag tgaatactgc agaccaatgt gctaatagat gtactaggaa taagggactt   240
ccattcactt gcaaggcttt tgttttttgat aaagcaagaa acaatgcct  ctggttcccc   300 ttcaatagca tgtcaagtgg agtgaaaaaa gaatttggcc atgaatttga cctctatgaa   360
aacaaagact acattagaaa ctgcatcatt ggtaaaggac gcagctacaa gggaacagta   420
tctatcacta gagtggcat  caaatgtcag ccctggagtt ccatgatacc acacgaacac   480
aggtaagaac agtatgaaga aaagagatga agcctctgtc ttttttacat gttaacagtc   540
tcatattagt ccttcagaat aattctacaa tcctaaaata acttagccaa cttgctgaat   600
tgtattacgg caaggtttat atgaattcat gactgatatt tagcaaatga ttaattaata   660
tgttaataaa atgtagccaa acaatatct  taccttaatg cctcaatttg tagatctcgg   720
tatttgtgga tcctattatg atcttttgtg taaagtctgg cagacaaatg caatatctaa   780
```

```
ttgttgagtc caatatcaca agcagtacaa aagtataaaa aagacttggc ctttctctaat    840
gtgttaaaat actttatgct ggtaataaca ctaagagtag ggcactagaa attttaagtg    900
aagataatgt gttgcagtta ctgcactcaa tggcttacta ttataaacca aaactgggat    960
cactaagctc cagtcagtca aaatgatcaa aattattgaa gagaataagc aattctgttc   1020
tttattagga cacagtagat acagactaca agtggagtg tgcttaataa gaggtagcat    1080
ttgttaagtg tcaattactc tattatccct tggagcttct caaaataacc atataaggtg   1140
taagatgtta aaggttatgg ttacactcag tgcacaggta agctaatagg ctgagagaag   1200
ctaaattact tactggggtc tcacagtaag aaagtgagct gaagtttcag cccagattta   1260
actggattct gggctcttta ttcatgttac ttcatgaatc tgtttctcaa ttgtgcagaa   1320
aaaagggggc tatttataag aaaagcaata acaaacaag taatgatctc aaataagtaa    1380
tgcaagaaat agtgagattt caaaatcagt ggcagcgatt tctcagttct gtcctaagtg   1440
gccttgctca atcacctgct atcttttagt ggagctttga attatgtttt cagacaactt   1500
cgattcagtt ctagaatgtt tgactcagca aattcacagg ctcatctttc taacttgatg   1560
gtgaatatgg aaattcagct aaatggatgt taataaaatt caaacgtttt aaggacagat   1620
ggaaatgaca gaattttaag gtaaaatata tgaaggaata taagataaag gatttttcta   1680
ccttcagcaa aaacataccc actaattagt aaaattaata ggcgaaaaaa agttgcatgc   1740
tcttatactg taatgattat catttttaaaa ctagcttttt gccttcgagc tatcggggta   1800
aagacctaca ggaaaactac tgtcgaaatc ctcgagggga agaaggggga ccctggtgtt   1860
tcacaagcaa tccagaggta cgctacgaag tctgtgacat tcctcagtgt tcagaagttg   1920
aatgcatgac ctgcaatggg gagagttatc gaggtctcat ggatcataca gaatcaggca   1980
agatttgtca gcgctgggat catcagacac cacaccggca caaattcttg cctgaaagat   2040
atcccgacaa gggctttgat gataattatt gccgcaatcc cgatggccag ccgaggccat   2100
ggtgctatac tcttgacct cacacccgct gggagtactg tgcaattaaa acatgcgctg    2160
acaatactat gaatgacact gatgttcctt tggaaacaac tgaatgcatc caaggtcaag   2220
gagaaggcta caggggcact gtcaatacca tttggaatgg aattccatgt cagcgttggg   2280
attctcagta tcctcacgag catgacatga ctcctgaaaa tttcaagtgc aaggacctac   2340
gagaaaatta ctgccgaaat ccagatgggt ctgaatcacc tggtgttttt accactgatc   2400
caaacatccg agttggctac tgctcccaaa ttccaaactg tgatatgtca catggacaag   2460
attgttatcg tgggaatggc aaaaattata tgggcaactt atcccaaaca agatctggac   2520
taacatgttc aatgtgggac aagaacatgg aagacttaca tcgtcatatc ttctgggaac   2580
cagatgcaag taagctgaat gagaattact gccgaaatcc agatgatgat gctcatggac   2640
cctggtgcta cacgggaaat ccactcattc cttgggatta ttgccctatt tctcgttgtg   2700
aaggtgatac cacacctaca atagtcaatt tagaccatcc cgtaatatct tgtgccaaaa   2760
cgaaacaatt gcgagttgta atgggattc caacacgaac aaacatagga tggatggtta   2820
gtttgagata cagaaataaa catatctgcg gaggatcatt gataaggag agttgggttc    2880
ttactgcacg acagtgtttc ccttctcgag acttgaaaga ttatgaagct tggcttggaa   2940
ttcatgatgt ccacggaaga ggagatgaga aatgcaaaca ggttctcaat gtttcccagc   3000
tggtatatgg ccctgaagga tcagatctgg ttttaatgaa gcttgccagg cctgctgtcc   3060
tggatgattt tgttagtacg attgatttac ctaattatgg atgcacaatt cctgaaaaga   3120
```

| | |
|---|---:|
| ccagttgcag tgtttatggc tggggctaca ctggattgat caactatgat ggcctattac | 3180 |
| gagtggcaca tctctatata atgggaaatg agaaatgcag ccagcatcat cgagggaagg | 3240 |
| tgactctgaa tgagtctgaa atatgtgctg gggctgaaaa gattggatca ggaccatgtg | 3300 |
| aggggggatta tggtggccca cttgtttgtg agcaacataa aatgagaatg gttcttggtg | 3360 |
| tcattgttcc tggtcgtgga tgtgccattc caaatcgtcc tggtattttt gtccgagtag | 3420 |
| catattatgc aaaatggata cacaaaatta ttttaacata aaggtaccaa cagtcatag | 3479 |

```
<210> SEQ ID NO 3
<211> LENGTH: 3279
<212> TYPE: DNA
<213> ORGANISM: Artificial Sequence
<220> FEATURE:
<223> OTHER INFORMATION: HGF-X7-d2

<400> SEQUENCE: 3
```

| | |
|---|---:|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggactt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caatgtcag ccctggagtt ccatgatacc acacgaacac | 480 |
| aggtaagaac agtatgaaga aaagagatga agcctctgtc ttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa aacaatatct taccttaatg cctcaatttg tagatctcgg | 720 |
| tatttgtgga tcctttacta ttataaacca aaactgggat cactaagctc agtcagtca | 780 |
| aaatgatcaa aattattgaa gagaataagc aattctgttc tttattagga cacagtagat | 840 |
| acagactaca aagtggagtg tgcttaataa gaggtagcat ttgttaagtg tcaattactc | 900 |
| tattatccct tggagcttct caaaataacc atataaggtg taagatgtta aaggttatgg | 960 |
| ttacactcag tgcacaggta agctaatagg ctgagagaag ctaaattact tactggggtc | 1020 |
| tcacagtaag aaagtgagct gaagtttcag cccagattta actggattct gggctcttta | 1080 |
| ttcatgttac ttcatgaatc tgtttctcaa ttgtgcagaa aaaggggc tatttataag | 1140 |
| aaaagcaata aacaaacaag taatgatctc aaataagtaa tgcaagaaat agtgagattt | 1200 |
| caaaatcagt ggcagcgatt tctcagttct gtcctaagtg gccttgctca atcacctgct | 1260 |
| atcttttagt ggagctttga aattatgttt cagacaactt cgattcagtt ctagaatgtt | 1320 |
| tgactcagca aattcacagg ctcatctttc taacttgatg gtgaatatgg aaattcagct | 1380 |
| aaatggatgt taataaaatt caaacgtttt aaggacagat ggaaatgaca gaattttaag | 1440 |
| gtaaaatata tgaaggaata taagataaag gatttttcta ccttcagcaa aaacataccc | 1500 |
| actaattagt aaaattaata ggcgaaaaaa agttgcatgc tcttatactg taatgattat | 1560 |
| catttttaaaa ctagcttttt gccttcgagc tatcggggta aagacctaca ggaaaactac | 1620 |
| tgtcgaaatc ctcgagggga agaagggga ccctggtgtt tcacaagcaa tccagaggta | 1680 |
| cgctacgaag tctgtgacat tcctcagtgt tcagaagttg aatgcatgac ctgcaatggg | 1740 |

-continued

```
gagagttatc gaggtctcat ggatcataca gaatcaggca agatttgtca gcgctgggat    1800
catcagacac cacaccggca caaattcttg cctgaaagat atcccgacaa gggcttttgat   1860 gataattatt gccgcaatcc cgatggccag ccgaggccat ggtgctatac tcttgaccct    1920
cacacccgct gggagtactg tgcaattaaa acatgcgctg acaatactat gaatgacact    1980
gatgttcctt tggaaacaac tgaatgcatc caaggtcaag agaaggcta caggggcact     2040 gtcaatacca tttggaatgg aattccatgt cagcgttggg attctcagta tcctcacgag    2100
catgacatga ctcctgaaaa tttcaagtgc aaggacctac gagaaaatta ctgccgaaat    2160
ccagatgggt ctgaatcacc ctggtgtttt accactgatc aaacatccg agttggctac     2220 tgctcccaaa ttccaaactg tgatatgtca catggacaag attgttatcg tgggaatggc    2280
aaaaattata tgggcaactt atcccaaaca agatctggac taacatgttc aatgtgggac    2340
aagaacatgg aagacttaca tcgtcatatc ttctgggaac cagatgcaag taagctgaat    2400
gagaattact gccgaaatcc agatgatgat gctcatggac cctggtgcta cacgggaaat    2460
ccactcattc cttgggatta ttgccctatt tctcgttgtg aaggtgatac cacacctaca    2520
atagtcaatt tagaccatcc cgtaatatct tgtgccaaaa cgaaacaatt gcgagttgta    2580
aatgggattc caacacgaac aaacatagga tggatggtta gtttgagata cagaaataaa    2640
catatctgcg gaggatcatt gataaaggag agttgggttc ttactgcacg acagtgtttc    2700
ccttctcgag acttgaaaga ttatgaagct tggcttggaa ttcatgatgt ccacggaaga    2760
ggagatgaga aatgcaaaca ggttctcaat gtttcccagc tggtatatgg ccctgaagga    2820
tcagatctgg ttttaatgaa gcttgccagg cctgctgtcc tggatgattt tgttagtacg    2880
attgatttac ctaattatgg atgcacaatt cctgaaaaga ccagttgcag tgtttatggc    2940
tggggctaca ctgggattgat caactatgat ggcctattac gagtggcaca tctctatata    3000
atgggaaatg agaaatgcag ccagcatcat cgagggaagg tgactctgaa tgagtctgaa    3060
atatgtgctg gggctgaaaa gattggatca ggaccatgtg agggggatta tggtggccca    3120 cttgttgtg agcaacataa aatgagaatg gttcttggtg tcattgttcc tggtcgtgga    3180
tgtgccattc caaatcgtcc tggtatttt gtccgagtag catattatgc aaaatggata    3240
cacaaaatta ttttaacata taaggtacca cagtcatag                           3279
```

<210> SEQ ID NO 4
<211> LENGTH: 3079
<212> TYPE: DNA
<213> ORGANISM: Artificial Sequence
<220> FEATURE:
<223> OTHER INFORMATION: HGF-X7-d3

<400> SEQUENCE: 4

```
atgtgggtga ccaaactcct gccagccctg ctgctgcagc atgtcctcct gcatctcctc     60
ctgctcccca tcgccatccc ctatgcagag ggacaaagga aaagaagaaa tacaattcat    120
gaattcaaaa atcagcaaa gactacccta atcaaatag atccagcact gaagataaaa     180
accaaaaaag tgaatactgc agaccaatgt gctaatagat gtactaggaa taaaggactt    240
ccattcactt gcaaggcttt tgtttttgat aaagcaagaa acaatgcct ctggttcccc    300 ttcaatagca tgtcaagtgg agtgaaaaaa gaatttggcc atgaatttga cctctatgaa    360
aacaaagact acattagaaa ctgcatcatt ggtaaaggac gcagctacaa gggaacagta    420
tctatcacta gagtggcat caaatgtcag ccctggagtt ccatgatacc acacgaacac    480
```

```
aggtaagaac agtatgaaga aaagagatga agcctctgtc ttttttacat gttaacagtc    540
tcatattagt ccttcagaat aattctacaa tcctaaaata acttagccaa cttgctgaat    600
tgtattacgg caaggtttat atgaattcat gactgatatt tagcaaatga ttaattaata    660
tgttaataaa atgtagccaa aacaatatct taccttaatg cctcaatttg tagatctcgg    720
tatttgtgga tcctaaggtg taagatgtta aaggttatgg ttacactcag tgcacaggta    780
agctaatagg ctgagagaag ctaaattact tactggggtc tcacagtaag aaagtgagct    840
gaagtttcag cccagattta actggattct gggctcttta ttcatgttac ttcatgaatc    900
tgtttctcaa ttgtgcagaa aaaggggggc tatttataag aaaagcaata aacaaacaag    960
taatgatctc aaataagtaa tgcaagaaat agtgagattt caaaatcagt ggcagcgatt   1020
tctcagttct gtcctaagtg gccttgctca atcacctgct atcttttagt ggagctttga   1080
aattatgttt cagacaactt cgattcagtt ctagaatgtt tgactcagca aattcacagg   1140
ctcatctttc taacttgatg gtgaatatgg aaattcagct aaatggatgt taataaaatt   1200
caaacgtttt aaggacagat ggaaatgaca gaattttaag gtaaaatata tgaaggaata   1260
taagataaag gattttttcta ccttcagcaa aaacatacccc actaattagt aaaattaata   1320
ggcgaaaaaa agttgcatgc tcttatactg taatgattat cattttaaaa ctagcttttt   1380
gccttcgagc tatcggggta aagacctaca ggaaaactac tgtcgaaatc ctcgagggga   1440
agaaggggga ccctggtgtt tcacaagcaa tccagaggta cgctacgaag tctgtgacat   1500
tcctcagtgt tcagaagttg aatgcatgac ctgcaatggg gagagttatc gaggtctcat   1560
ggatcataca gaatcaggca agatttgtca gcgctgggat catcagacac cacaccggca   1620
caaattcttg cctgaaagat atcccgacaa gggctttgat gataattatt gccgcaatcc   1680
cgatggccag ccgaggccat ggtgctatac tcttgaccct cacacccgct gggagtactg   1740
tgcaattaaa acatgcgctg acaatactat gaatgacact gatgttcctt tggaaacaac   1800
tgaatgcatc caaggtcaag gagaaggcta caggggcact gtcaatacca tttgaatgg    1860 aattccatgt cagcgttggg attctcagta tcctcacgag catgacatga ctcctgaaaa   1920
tttcaagtgc aaggacctac gagaaaatta ctgccgaaat ccagatgggt ctgaatcacc   1980
ctggtgtttt accactgatc caaacatccg agttggctac tgctcccaaa ttccaaactg   2040
tgatatgtca catggacaag attgttatcg tgggaatggc aaaaattata tgggcaactt   2100
atcccaaaca agatctggac taacatgttc aatgtgggac aagaacatgg aagacttaca   2160
tcgtcatatc ttctgggaac cagatgcaag taagctgaat gagaattact gccgaaatcc   2220
agatgatgat gctcatggac cctggtgcta cacgggaaat ccactcattc cttgggatta   2280
ttgccctatt tctcgttgtg aaggtgatac cacacctaca atagtcaatt tagaccatcc   2340
cgtaatatct tgtgccaaaa cgaaacaatt gcgagttgta atgggattcc aacacgaac    2400 aaacatagga tggatggtta gtttgagata cagaaataaa catatctgcg gaggatcatt   2460
gataaaggag agttgggttc ttactgcacg acagtgtttc ccttctcgag acttgaaaga   2520
ttatgaagct tggcttggaa ttcatgatgt ccacggaaga ggagatgaga aatgcaaaca   2580
ggttctcaat gtttcccagc tggtatatgg ccctgaagga tcagatctgg ttttaatgaa   2640
gcttgccagg cctgctgtcc tggatgattt tgttagtacg attgatttac ctaattatgg   2700
atgcacaatt cctgaaaaga ccagttgcag tgtttatggc tggggctaca ctggattgat   2760
caactatgat ggcctattac gagtggcaca tctctatata atgggaaatg agaaatgcag   2820
ccagcatcat cgagggaagg tgactctgaa tgagtctgaa atatgtgctg ggctgaaaaa   2880
```

| | |
|---|---|
| gattggatca ggaccatgtg aggggggatta tggtggccca cttgtttgtg agcaacataa | 2940 |
| aatgagaatg gttcttggtg tcattgttcc tggtcgtgga tgtgccattc caaatcgtcc | 3000 |
| tggtattttt gtccgagtag catattatgc aaaatggata cacaaaatta ttttaacata | 3060 |
| taaggtacca cagtcatag | 3079 |

<210> SEQ ID NO 5
<211> LENGTH: 2879
<212> TYPE: DNA
<213> ORGANISM: Artificial Sequence
<220> FEATURE:
<223> OTHER INFORMATION: HGF-X7-d4

<400> SEQUENCE: 5

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactaccccta atcaaaatag atccagcact gaagataaaa | 180 |
| accaaaaaag tgaatactgc agaccaatgt gctaatagat gtactaggaa taaaggactt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc ttttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa acaatatct taccttaatg cctcaatttg tagatctcgg | 720 |
| tatttgtgga tccttataag aaaagcaata acaaacaag taatgatctc aaataagtaa | 780 |
| tgcaagaaat agtgagattt caaaatcagt ggcagcgatt tctcagttct gtcctaagtg | 840 |
| gccttgctca atcacctgct atcttttagt ggagctttga aattatgttt cagacaactt | 900 |
| cgattcagtt ctagaatgtt tgactcagca aattcacagg ctcatctttc taacttgatg | 960 |
| gtgaatatgg aaattcagct aaatggatgt taataaaatt caaacgtttt aaggacagat | 1020 |
| ggaaatgaca gaatttttaag gtaaaatata tgaaggaata taagataaag gatttttcta | 1080 |
| ccttcagcaa aaacataccc actaattagt aaaattaata ggcgaaaaaa agttgcatgc | 1140 |
| tcttatactg taatgattat cattttaaaa ctagcttttt gccttcgagc tatcggggta | 1200 |
| aagacctaca ggaaaactac tgtcgaaatc ctcgagggga agaaggggga ccctggtgtt | 1260 |
| tcacaagcaa tccagaggta cgctacgaag tctgtgacat cctcagtgt tcagaagttg | 1320 |
| aatgcatgac ctgcaatggg gagagttatc gaggtctcat ggatcataca gaatcaggca | 1380 |
| agatttgtca gcgctgggat catcagacac acaccggca caaattcttg cctgaaagat | 1440 |
| atcccgacaa gggctttgat gataattatt gccgcaatcc cgatggccag ccgaggccat | 1500 |
| ggtgctatac tcttgacccct cacacccgct gggagtactg tgcaattaaa acatgcgctg | 1560 |
| acaatactat gaatgacact gatgttcctt tggaaacaac tgaatgcatc caaggtcaag | 1620 |
| gagaaggcta caggggcact gtcaatacca tttggaatgg aattccatgt cagcgttggg | 1680 |
| attctcagta tcctcacgag catgacatga ctcctgaaaa tttcaagtgc aaggacctac | 1740 |
| gagaaaatta ctgccgaaat ccagatgggt ctgaatcacc ctggtgtttt accactgatc | 1800 |

```
caaacatccg agttggctac tgctcccaaa ttccaaactg tgatatgtca catggacaag    1860
attgttatcg tgggaatggc aaaaattata tgggcaactt atcccaaaca agatctggac    1920
taacatgttc aatgtgggac aagaacatgg aagacttaca tcgtcatatc ttctgggaac    1980
cagatgcaag taagctgaat gagaattact gccgaaatcc agatgatgat gctcatggac    2040
cctggtgcta cacgggaaat ccactcattc cttgggatta ttgccctatt tctcgttgtg    2100
aaggtgatac cacacctaca atagtcaatt tagaccatcc cgtaatatct tgtgccaaaa    2160
cgaaacaatt gcgagttgta atgggattc caacacgaac aaacatagga tggatggtta    2220
gtttgagata cagaaataaa catatctgcg gaggatcatt gataaaggag agttgggttc    2280
ttactgcacg acagtgtttc ccttctcgag acttgaaaga ttatgaagct tggcttggaa    2340
ttcatgatgt ccacggaaga ggagatgaga atgcaaaca ggttctcaat gtttcccagc    2400
tggtatatgg ccctgaagga tcagatctgg ttttaatgaa gcttgccagg cctgctgtcc    2460
tggatgattt tgttagtacg attgatttac taattatgg atgcacaatt cctgaaaaga    2520
ccagttgcag tgtttatggc tggggctaca ctggattgat caactatgat ggcctattac    2580
gagtggcaca tctctatata tgggaaatg agaaatgcag ccagcatcat cgagggaagg    2640
tgactctgaa tgagtctgaa atatgtgctg gggctgaaaa gattggatca ggaccatgtg    2700
agggggatta tggtggccca cttgtttgtg agcaacataa aatgagaatg gttcttggtg    2760
tcattgttcc tggtcgtgga tgtgccattc caaatcgtcc tggtattttt gtccgagtag    2820
catattatgc aaaatggata cacaaaatta ttttaacata aaggtacca cagtcatag     2879
```

<210> SEQ ID NO 6
<211> LENGTH: 3679
<212> TYPE: DNA
<213> ORGANISM: Artificial Sequence
<220> FEATURE:
<223> OTHER INFORMATION: HGF-X7

<400> SEQUENCE: 6

```
atgtgggtga ccaaactcct gccagccctg ctgctgcagc atgtcctcct gcatctcctc      60
ctgctcccca tcgccatccc ctatgcagag ggacaaagga aaagaagaaa tacaattcat     120
gaattcaaaa aatcagcaaa gactacccta atcaaaatag atccagcact gaagataaaa     180
accaaaaaag tgaatactgc agaccaatgt gctaatagat gtactaggaa taaggacttc     240
ccattcactt gcaaggcttt tgttttttgat aaagcaagaa acaatgcct ctggttcccc     300 ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta gagtggcat caaatgtcag ccctggagtt ccatgatacc acacgaacac     480
aggtaagaac agtatgaaga aaagagatga agcctctgtc tttttacat gttaacagtc     540 tcatattagt ccttcagaat aattctacaa tcctaaaata acttagccaa cttgctgaat     600
tgtattacgg caaggtttat atgaattcat gactgatatt tagcaaatga ttaattaata     660
tgttaataaa atgtagccaa acaatatct taccttaatg cctcaatttg tagatctcgg     720
tatttgtgga tcctgggtag gaaacacatt tgaatggtat ttactaagat actaaaatcc     780
ttggacttca ctctaatttt agtgccattt agaactcaag gtctcagtaa agtagaaat      840 aaagcctgtt aacaaaacac aaactgaata ttaaaaatgt aactggattt tcaaagaaat     900
gtttactggt attacctgta gatgtatat ctttattatg atcttttgtg taaagtctgg      960
cagacaaatg caatatctaa ttgttgagtc caatatcaca agcagtacaa aagtataaaa    1020
```

```
aagacttggc cttttctaat gtgttaaaat actttatgct ggtaataaca ctaagagtag    1080
ggcactagaa attttaagtg aagataatgt gttgcagtta ctgcactcaa tggcttacta    1140
ttataaacca aaactgggat cactaagctc cagtcagtca aaatgatcaa aattattgaa    1200
gagaataagc aattctgttc tttattagga cacagtagat acagactaca aagtggagtg    1260
tgcttaataa gaggtagcat ttgttaagtg tcaattactc tattatccct tggagcttct    1320
caaaataacc ataaaggtg taagatgtta aaggttatgg ttacactcag tgcacaggta     1380
agctaatagg ctgagagaag ctaaattact tactggggtc tcacagtaag aaagtgagct    1440
gaagtttcag cccagattta actggattct gggctcttta ttcatgttac ttcatgaatc    1500
tgtttctcaa ttgtgcagaa aaaggggggc tatttataag aaaagcaata aacaaacaag    1560
taatgatctc aaataagtaa tgcaagaaat agtgagattt caaaatcagt ggcagcgatt    1620
tctcagttct gtcctaagtg gccttgctca atcacctgct atcttttagt ggagctttga    1680
aattatgttt cagacaactt cgattcagtt ctagaatgtt tgactcagca aattcacagg    1740
ctcatctttc taacttgatg gtgaatatgg aaattcagct aaatggatgt taataaaatt    1800
caaacgtttt aaggacagat ggaaatgaca gaattttaag gtaaaatata tgaaggaata    1860
taagataaag gatttttcta ccttcagcaa aaacataccc actaattagt aaaattaata    1920
ggcgaaaaaa agttgcatgc tcttatactg taatgattat cattttaaaa ctagcttttt    1980
gccttcgagc tatcggggta aagacctaca ggaaaactac tgtcgaaatc ctcgagggga    2040
agaaggggga ccctggtgtt tcacaagcaa tccagaggta cgctacgaag tctgtgacat    2100
tcctcagtgt tcagaagttg aatgcatgac ctgcaatggg gagagttatc gaggtctcat    2160
ggatcataca gaatcaggca agatttgtca gcgctgggat catcagacac cacaccggca    2220
caaattcttg cctgaaagat atcccgacaa gggctttgat gataattatt gccgcaatcc    2280
cgatggccag ccgaggccat ggtgctatac tcttgacccct cacacccgct gggagtactg    2340
tgcaattaaa acatgcgctg acaatactat gaatgacact gatgttcctt tggaaacaac    2400
tgaatgcatc caaggtcaag gagaaggcta caggggcact gtcaatacca tttggaatgg    2460
aattccatgt cagcgttggg attctcagta tcctcacgag catgacatga ctcctgaaaa    2520
tttcaagtgc aaggacctac gagaaaatta ctgccgaaat ccagatgggt ctgaatcacc    2580
ctggtgtttt accactgatc caaacatccg agttggctac tgctcccaaa ttccaaactg    2640
tgatatgtca catggacaag attgttatcg tgggaatggc aaaaattata tgggcaactt    2700
atcccaaaca agatctggac taacatgttc aatgtgggaa aagaacatgg aagacttaca    2760
tcgtcatatc ttctgggaac cagatgcaag taagctgaat gagaattact gccgaaatcc    2820
agatgatgat gctcatggac cctggtgcta cacgggaaat ccactcattc cttgggatta    2880
ttgccctatt tctcgttgtg aaggtgatac cacacctaca atagtcaatt tagaccatcc    2940
cgtaatatct tgtgccaaaa cgaaacaatt gcgagttgta atgggattca acacgaac     3000 aaacatagga tggatggtta gtttgagata cagaaataaa catatctgcg gaggatcatt    3060
gataaaggag agttgggttc ttactgcacg acagtgtttc ccttctcgag acttgaaaga    3120
ttatgaagct tggcttggaa ttcatgatgt ccacggaaga ggagatgaga atgcaaaca    3180 ggttctcaat gtttcccagc tggtatatgg ccctgaagga tcagatctgg ttttaatgaa    3240
gcttgccagg cctgctgtcc tgcatgattt tgtgagtacg attgatttac ctaattatgg    3300
atgcacaatt cctgaaaaga ccagttgcag tgtttatggc tggggctaca ctggattgat    3360
```

| | |
|---|---|
| caactatgat ggcctattac gagtggcaca tctctatata atgggaaatg agaaatgcag | 3420 |
| ccagcatcat cgagggaagg tgactctgaa tgagtctgaa atatgtgctg ggctgaaaa | 3480 |
| gattggatca ggaccatgtg aggggatta tggtggccca cttgtttgtg agcaacataa | 3540 |
| aatgagaatg gttcttggtg tcattgttcc tggtcgtgga tgtgccattc caaatcgtcc | 3600 |
| tggtattttt gtccgagtag catattatgc aaaatggata cacaaaatta ttttaacata | 3660 |
| taaggtacca cagtcatag | 3679 |

<210> SEQ ID NO 7
<211> LENGTH: 2730
<212> TYPE: DNA
<213> ORGANISM: Artificial Sequence
<220> FEATURE:
<223> OTHER INFORMATION: HGF-X8

<400> SEQUENCE: 7

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggactt | 240 |
| ccattcactt gcaaggcttt tgttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |
| tctatcacta gagtggcat caaatgtcag ccctggagtt ccatgatacc acacgaacac | 480 |
| aggtaagaac agtatgaaga aaagagatga agcctctgtc tttttacat gttaacagtc | 540 |
| tcatattagt ccttcagaat aattctacaa tcctaaaata acttagccaa cttgctgaat | 600 |
| tgtattacgg caaggtttat atgaattcat gactgatatt tagcaaatga ttaattaata | 660 |
| tgttaataaa atgtagccaa aacaatatct taccttaatg cctcaatttg tagatctcgg | 720 |
| tatttgtgga tccttatgtt tcagacaact tcgattcagt tctagaatgt ttgactcagc | 780 |
| aaattcacag gctcatcttt ctaacttgat ggtgaatatg gaaattcagc taaatggatg | 840 |
| ttaataaaat tcaaacgttt taaggacaga tggaaatgac agaatttaa ggtaaaatat | 900 |
| atgaaggaat ataagataaa ggattttct accttcagca aaaacatacc cactaattag | 960 |
| taaaattaat aggcgaaaaa aagttgcatg ctcttatact gtaatgatta tcattttaaa | 1020 |
| actagctttt tgccttcgag ctatcggggt aaagacctac aggaaaacta ctgtcgaaat | 1080 |
| cctcgagggg aagaagggg accctggtgt ttcacaagca atccagaggt acgctacgaa | 1140 |
| gtctgtgaca ttcctcagtg ttcagaagtt gaatgcatga cctgcaatgg ggagagttat | 1200 |
| cgaggtctca tggatcatac agaatcaggc aagatttgtc agcgctggga tcatcagaca | 1260 |
| ccacaccggc acaaattctt gcctgaaaga tatcccgaca agggctttga tgataattat | 1320 |
| tgccgcaatc ccgatggcca gccgaggcca tggtgctata ctcttgaccc tcacacccgc | 1380 |
| tgggagtact gtgcaattaa acatgcgct gacaatacta tgaatgacac tgatgttcct | 1440 |
| ttggaaacaa ctgaatgcat ccaaggtcaa ggagaaggct acaggggcac tgtcaatacc | 1500 |
| atttggaatg gaattccatg tcagcgttgg gattctcagt atcctcacga gcatgacatg | 1560 |
| actcctgaaa atttcaagtg caaggaccta cgagaaaatt actgccgaaa tccagatggg | 1620 |
| tctgaatcac cctggtgttt taccactgat ccaaacatcc gagttggcta ctgctcccaa | 1680 |
| attccaaact gtgatatgtc acatggacaa gattgttatc gtgggaatgg caaaaattat | 1740 |

```
atgggcaact tatcccaaac aagatctgga ctaacatgtt caatgtggga caagaacatg     1800
gaagacttac atcgtcatat cttctgggaa ccagatgcaa gtaagctgaa tgagaattac     1860
tgccgaaatc cagatgatga tgctcatgga ccctggtgct acacgggaaa tccactcatt     1920
ccttgggatt attgccctat ttctcgttgt gaaggtgata ccacacctac aatagtcaat     1980
ttagaccatc ccgtaatatc ttgtgccaaa acgaaacaat tgcgagttgt aaatgggatt     2040
ccaacacgaa caaacatagg atggatggtt agtttgagat acagaaataa acatatctgc     2100
ggaggatcat tgataaagga gagttgggtt cttactgcac gacagtgttt cccttctcga     2160
gacttgaaag attatgaagc ttggcttgga attcatgatg tccacggaag aggagatgag     2220
aaatgcaaac aggttctcaa tgtttcccag ctggtatatg gccctgaagg atcagatctg     2280
gttttaatga gcttgccag gcctgctgtc tggatgatt tgttagtac gattgattta       2340 cctaattatg gatgcacaat tcctgaaaag accagttgca gtgtttatgg ctggggctac     2400
actggattga tcaactatga tggcctatta cgagtggcac atctctatat aatgggaaat     2460
gagaaatgca gccagcatca tcgagggaag gtgactctga atgagtctga aatatgtgct     2520
ggggctgaaa agattggatc aggaccatgt gaggggatt atggtggccc acttgtttgt     2580
gagcaacata aaatgagaat ggttcttggt gtcattgttc ctggtcgtgg atgtgccatt     2640
ccaaatcgtc ctggtatttt tgtccgagta gcatattatg caaaatggat acacaaaatt     2700
attttaacat ataaggtacc acagtcatag                                     2730

<210> SEQ ID NO 8
<211> LENGTH: 40
<212> TYPE: DNA
<213> ORGANISM: Artificial Sequence
<220> FEATURE:
<223> OTHER INFORMATION: d1 forward primer

<400> SEQUENCE: 8
tctcggtatt tgtggatcct attatgatct tttgtgtaaa                           40

<210> SEQ ID NO 9
<211> LENGTH: 40
<212> TYPE: DNA
<213> ORGANISM: Artificial Sequence
<220> FEATURE:
<223> OTHER INFORMATION: d1 reverse primer

<400> SEQUENCE: 9
tttacacaaa agatcataat aggatccaca ataccgaga                            40

<210> SEQ ID NO 10
<211> LENGTH: 40
<212> TYPE: DNA
<213> ORGANISM: Artificial Sequence
<220> FEATURE:
<223> OTHER INFORMATION: d2 forward primer

<400> SEQUENCE: 10
tctcggtatt tgtggatcct ttactattat aaaccaaaac                           40

<210> SEQ ID NO 11
<211> LENGTH: 40
<212> TYPE: DNA
<213> ORGANISM: Artificial Sequence
<220> FEATURE:
<223> OTHER INFORMATION: d2 reverse primer
```

```
<400> SEQUENCE: 11
gttttggttt ataatagtaa aggatccaca ataccgaga                40

<210> SEQ ID NO 12
<211> LENGTH: 40
<212> TYPE: DNA
<213> ORGANISM: Artificial Sequence
<220> FEATURE:
<223> OTHER INFORMATION: d3 forward primer

<400> SEQUENCE: 12
tctcggtatt tgtggatcct aaggtgtaag atgttaaagg               40

<210> SEQ ID NO 13
<211> LENGTH: 40
<212> TYPE: DNA
<213> ORGANISM: Artificial Sequence
<220> FEATURE:
<223> OTHER INFORMATION: d3 reverse primer

<400> SEQUENCE: 13
cctttaacat cttacacctt aggatccaca ataccgaga                40

<210> SEQ ID NO 14
<211> LENGTH: 40
<212> TYPE: DNA
<213> ORGANISM: Artificial Sequence
<220> FEATURE:
<223> OTHER INFORMATION: d4 forward primer

<400> SEQUENCE: 14
tctcggtatt tgtggatcct tataagaaaa gcaataaaca               40

<210> SEQ ID NO 15
<211> LENGTH: 40
<212> TYPE: DNA
<213> ORGANISM: Artificial Sequence
<220> FEATURE:
<223> OTHER INFORMATION: d4 reverse primer

<400> SEQUENCE: 15
tgtttattgc ttttcttata aggatccaca ataccgaga                40
```